(12) United States Patent
Scott et al.

(10) Patent No.: US 10,682,046 B2
(45) Date of Patent: Jun. 16, 2020

(54) SURGICAL SYSTEM WITH HERMETICALLY SEALED ENDOSCOPE

(71) Applicant: INTUITIVE SURGICAL OPERATIONS, INC., Sunnyvale, CA (US)

(72) Inventors: David D. Scott, Oakland, CA (US); David C. Shafer, Menlo Park, CA (US); Dominique Brichard, San Jose, CA (US); Peter M. Herzlinger, Saratoga, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 87 days.

(21) Appl. No.: 15/953,517

(22) Filed: Apr. 16, 2018

(65) Prior Publication Data
US 2018/0228351 A1    Aug. 16, 2018

Related U.S. Application Data

(63) Continuation of application No. 15/394,703, filed on Dec. 29, 2016, now Pat. No. 9,962,069, which is a
(Continued)

(51) Int. Cl.
*A61B 1/06* (2006.01)
*H04N 13/204* (2018.01)
(Continued)

(52) U.S. Cl.
CPC ............ *A61B 1/06* (2013.01); *A61B 1/00009* (2013.01); *A61B 1/0011* (2013.01);
(Continued)

(58) Field of Classification Search
CPC ........... A61B 1/06; A61B 1/121; A61B 1/125; A61B 1/042; A61B 1/00142; A61L 2/07
(Continued)

(56) References Cited

U.S. PATENT DOCUMENTS

| 3,499,107 A | 3/1970 | Sheldon |
| 3,520,587 A | 7/1970 | Tasaki et al. |

(Continued)

FOREIGN PATENT DOCUMENTS

| WO | WO-199727798 A1 | 8/1997 | |
| WO | WO-2013059821 A2 * | 4/2013 | ............... A61B 1/07 |

(Continued)

OTHER PUBLICATIONS

G Dogangil et al., A Review of Medical Robotics for minimally invasive soft tissue surgery, Dept. Mechanical Engr. Imperial College London, UK, IMechE vol. 224 Part H: J. Engineering in Medicine, May 19, 2009, 27 pages (Year: 2009).*

(Continued)

*Primary Examiner* — Clayton E. LaBalle
*Assistant Examiner* — Kevin C Butler

(57) ABSTRACT

In one embodiment, a minimally invasive surgical system includes a patient side manipulator, a hermetically sealed endoscopic camera instrument, a vision cart, and a monitor. The patient side manipulator has a robotic arm. The endoscopic camera instrument has a housing at a proximal end to couple to the robotic arm. The endoscopic camera instrument further has a hermetically sealed camera sensor at a distal end, a shaft coupled to the housing, and a wristed joint coupled between the shaft and the camera sensor. The vision cart has a camera control unit coupled in communication with the hermetically sealed camera sensor to capture the images of the surgical site. The monitor is coupled in communication with the camera control unit to display the captured images of the surgical site.

20 Claims, 16 Drawing Sheets

Related U.S. Application Data continuation of application No. 15/018,867, filed on Feb. 9, 2016, now Pat. No. 9,565,997, which is a continuation of application No. 14/662,083, filed on Mar. 18, 2015, now Pat. No. 9,271,633, which is a continuation of application No. 14/030,122, filed on Sep. 18, 2013, now Pat. No. 9,005,113, which is a continuation of application No. 12/780,898, filed on May 15, 2010, now Pat. No. 8,556,807, which is a continuation-in-part of application No. 11/614,661, filed on Dec. 21, 2006, now Pat. No. 8,814,779.

(51) Int. Cl.
| | | |
|---|---|---|
| *G02B 23/24* | (2006.01) | |
| *A61B 1/00* | (2006.01) | |
| *A61B 1/045* | (2006.01) | |
| *A61B 1/313* | (2006.01) | |
| *G02B 13/00* | (2006.01) | |
| *H04N 5/225* | (2006.01) | |
| *A61B 1/05* | (2006.01) | |
| *A61B 34/37* | (2016.01) | |
| *A61B 90/00* | (2016.01) | |
| *A61B 90/50* | (2016.01) | |
| *A61B 34/30* | (2016.01) | |
| *H04N 13/20* | (2018.01) | |

(52) U.S. Cl.
CPC ...... *A61B 1/00096* (2013.01); *A61B 1/00105* (2013.01); *A61B 1/00114* (2013.01); *A61B 1/00124* (2013.01); *A61B 1/00149* (2013.01); *A61B 1/00165* (2013.01); *A61B 1/00167* (2013.01); *A61B 1/00193* (2013.01); *A61B 1/045* (2013.01); *A61B 1/051* (2013.01); *A61B 1/0684* (2013.01); *A61B 1/313* (2013.01); *A61B 1/3132* (2013.01); *G02B 13/0015* (2013.01); *G02B 23/2415* (2013.01); *G02B 23/2476* (2013.01); *H04N 5/2254* (2013.01); *H04N 13/204* (2018.05); *A61B 1/00* (2013.01); *A61B 34/30* (2016.02); *A61B 34/37* (2016.02); *A61B 90/361* (2016.02); *A61B 90/50* (2016.02); *A61B 2034/302* (2016.02); *G02B 13/00* (2013.01); *G02B 23/24* (2013.01); *H04N 5/225* (2013.01); *H04N 13/20* (2018.05); *H04N 2005/2255* (2013.01)

(58) Field of Classification Search
USPC ........................................................ 600/133
See application file for complete search history.

(56) References Cited

U.S. PATENT DOCUMENTS

| | | | |
|---|---|---|---|
| 3,534,729 A | 10/1970 | Sakamoto | |
| 3,788,303 A * | 1/1974 | Hall ................. | A61B 1/0052 600/148 |
| 4,473,841 A | 9/1984 | Murakoshi et al. | |
| 4,483,326 A * | 11/1984 | Yamaka ............ | A61B 1/0057 600/141 |
| 4,491,865 A | 1/1985 | Danna et al. | |
| 4,573,450 A | 3/1986 | Arakawa | |
| 4,604,992 A | 8/1986 | Sato | |
| 4,682,219 A | 7/1987 | Arakawa | |
| 4,692,608 A | 9/1987 | Cooper et al. | |
| 4,697,210 A | 9/1987 | Toyota et al. | |
| 4,779,130 A | 10/1988 | Yabe | |
| 4,779,613 A | 10/1988 | Hashiguchi et al. | |
| 4,832,003 A * | 5/1989 | Yabe ................. | A61B 1/051 348/65 |
| 4,834,069 A * | 5/1989 | Umeda .............. | A61B 1/0055 138/120 |
| 4,867,138 A | 9/1989 | Kubota et al. | |
| 4,873,572 A * | 10/1989 | Miyazaki .......... | A61B 1/00193 348/45 |
| 4,878,485 A | 11/1989 | Adair | |
| 4,918,521 A | 4/1990 | Yabe | |
| 4,924,853 A | 5/1990 | Jones, Jr. et al. | |
| 5,051,823 A | 9/1991 | Cooper et al. | |
| 5,051,824 A | 9/1991 | Nishigaki | |
| RE33,854 E | 3/1992 | Adair | |
| 5,096,292 A | 3/1992 | Sakamoto et al. | |
| 5,122,650 A | 6/1992 | McKinley | |
| 5,124,838 A | 6/1992 | Forkey et al. | |
| 5,166,787 A | 11/1992 | Irion | |
| 5,188,094 A | 2/1993 | Adair | |
| 5,191,203 A | 3/1993 | McKinley | |
| 5,212,595 A | 5/1993 | Dennison, Jr. et al. | |
| 5,228,430 A | 7/1993 | Sakamoto | |
| 5,237,446 A | 8/1993 | Takahashi | |
| 5,299,559 A * | 4/1994 | Bruce ............... | A61B 1/0052 600/141 |
| 5,305,121 A | 4/1994 | Moll | |
| 5,349,137 A | 9/1994 | Cedrone | |
| 5,377,669 A | 1/1995 | Schulz | |
| 5,381,784 A | 1/1995 | Adair | |
| 5,419,313 A | 5/1995 | Lemke | |
| 5,430,475 A | 7/1995 | Goto et al. | |
| 5,448,989 A * | 9/1995 | Heckele ........... | A61B 1/0055 600/104 |
| 5,454,827 A * | 10/1995 | Aust ................. | A61B 17/29 600/564 |
| 5,494,483 A | 2/1996 | Adair | |
| 5,536,244 A | 7/1996 | Muller et al. | |
| 5,557,454 A | 9/1996 | Takahashi | |
| 5,577,991 A | 11/1996 | Akui et al. | |
| 5,587,736 A | 12/1996 | Walls | |
| 5,588,948 A | 12/1996 | Takahashi et al. | |
| 5,599,278 A | 2/1997 | Hibbard | |
| 5,603,687 A | 2/1997 | Hori et al. | |
| 5,609,561 A | 3/1997 | Uehara et al. | |
| 5,635,301 A | 6/1997 | Kondo et al. | |
| 5,673,147 A | 9/1997 | McKinley | |
| 5,743,846 A | 4/1998 | Takahashi et al. | |
| 5,810,713 A | 9/1998 | Rondeau et al. | |
| 5,835,133 A | 11/1998 | Moreton | |
| 5,841,126 A | 11/1998 | Fossum et al. | |
| 5,860,912 A | 1/1999 | Chiba | |
| 5,864,359 A | 1/1999 | Kazakevich | |
| 5,868,664 A | 2/1999 | Speier et al. | |
| 5,929,901 A | 7/1999 | Adair | |
| 5,940,126 A | 8/1999 | Kimura | |
| 5,949,483 A | 9/1999 | Fossum et al. | |
| 5,971,915 A | 10/1999 | Yamamoto et al. | |
| 5,986,693 A | 11/1999 | Adair et al. | |
| 5,990,469 A | 11/1999 | Bechtel et al. | |
| 6,030,339 A | 2/2000 | Tatsuno et al. | |
| 6,043,839 A | 3/2000 | Adair et al. | |
| 6,080,101 A | 6/2000 | Tatsuno et al. | |
| 6,142,932 A | 11/2000 | Morizumi | |
| 6,144,762 A | 11/2000 | Brooks | |
| 6,146,326 A | 11/2000 | Pollack et al. | |
| 6,149,582 A | 11/2000 | Morizumi | |
| 6,166,768 A | 12/2000 | Fossum et al. | |
| 6,191,809 B1 | 2/2001 | Hori et al. | |
| 6,211,904 B1 | 4/2001 | Adair et al. | |
| 6,223,100 B1 * | 4/2001 | Green ............... | H04N 13/398 700/264 |
| 6,228,468 B1 | 5/2001 | Vodrahalli | |
| 6,270,453 B1 * | 8/2001 | Sakai ................ | A61B 1/0055 600/141 |
| 6,275,255 B1 | 8/2001 | Adair et al. | |
| 6,310,642 B1 | 10/2001 | Adair et al. | |
| 6,328,691 B1 | 12/2001 | Rudischhauser | |
| 6,390,972 B1 | 5/2002 | Speier et al. | |
| 6,419,626 B1 * | 7/2002 | Yoon ................ | A61B 1/00052 600/103 |
| 6,424,369 B1 | 7/2002 | Adair et al. | |

(56) References Cited

U.S. PATENT DOCUMENTS

| | | | |
|---|---|---|---|
| 6,425,857 B1 | 7/2002 | Rudischhauser et al. | |
| 6,436,107 B1* | 8/2002 | Wang | A61B 1/00149 318/568.11 |
| 6,450,950 B2 | 9/2002 | Irion | |
| 6,452,626 B1 | 9/2002 | Adair et al. | |
| 6,503,196 B1* | 1/2003 | Kehr | A61B 1/00096 600/129 |
| 6,547,722 B1 | 4/2003 | Higuma et al. | |
| 6,558,316 B2 | 5/2003 | Kikuchi et al. | |
| 6,572,536 B1 | 6/2003 | Bon et al. | |
| 6,572,537 B2 | 6/2003 | Futatsugi et al. | |
| 6,606,113 B2 | 8/2003 | Nakamura | |
| 6,614,595 B2 | 9/2003 | Igarashi | |
| 6,632,172 B1* | 10/2003 | Igarashi | A61B 1/00096 600/101 |
| 6,648,817 B2 | 11/2003 | Schara et al. | |
| 6,692,430 B2 | 2/2004 | Adler | |
| 6,692,431 B2 | 2/2004 | Kazakevich | |
| 6,716,161 B2 | 4/2004 | Higuma et al. | |
| 6,721,008 B2 | 4/2004 | Lee et al. | |
| 6,767,322 B1 | 7/2004 | Futatsugi et al. | |
| 6,817,974 B2* | 11/2004 | Cooper | A61B 17/00234 600/142 |
| 6,817,975 B1 | 11/2004 | Farr et al. | |
| 6,862,036 B2 | 3/2005 | Adair et al. | |
| 6,891,266 B2 | 5/2005 | Kinayman et al. | |
| 6,898,022 B2 | 5/2005 | Igarashi | |
| 6,932,760 B1 | 8/2005 | Pang et al. | |
| 6,955,644 B2 | 10/2005 | Forkey et al. | |
| 6,976,956 B2 | 12/2005 | Takahashi et al. | |
| 6,982,740 B2 | 1/2006 | Adair et al. | |
| 6,982,742 B2 | 1/2006 | Adair et al. | |
| 7,030,904 B2 | 4/2006 | Adair et al. | |
| 7,046,270 B2 | 5/2006 | Murata et al. | |
| 7,074,181 B2* | 7/2006 | Futatsugi | A61B 1/05 600/110 |
| 7,170,677 B1 | 1/2007 | Bendall et al. | |
| 7,410,462 B2 | 8/2008 | Navok et al. | |
| 7,852,371 B2 | 12/2010 | Konstorum et al. | |
| 8,144,409 B2 | 3/2012 | Lin et al. | |
| 8,219,178 B2* | 7/2012 | Smith | A61B 5/06 600/424 |
| 8,556,807 B2 | 10/2013 | Scott et al. | |
| 8,602,967 B2* | 12/2013 | Robertson | A61B 1/00096 600/103 |
| 8,633,975 B2* | 1/2014 | Amling | H04L 12/462 348/65 |
| 8,723,922 B2* | 5/2014 | Berger | H04N 13/211 348/46 |
| 8,814,779 B2 | 8/2014 | Shaper et al. | |
| 8,974,472 B2* | 3/2015 | Gal | A61B 17/221 606/127 |
| 9,005,113 B2 | 4/2015 | Scott et al. | |
| 9,118,850 B2* | 8/2015 | Luo | A61B 1/041 |
| 9,196,176 B2* | 11/2015 | Hager | G09B 7/00 |
| 9,271,633 B2 | 3/2016 | Scott et al. | |
| 9,486,189 B2* | 11/2016 | Oko | A61B 17/00234 |
| 9,565,997 B2 | 2/2017 | Scott et al. | |
| 9,621,825 B2* | 4/2017 | Luo | A61B 1/041 |
| 9,699,445 B2 | 7/2017 | Hoffman et al. | |
| 9,829,697 B2* | 11/2017 | Zobel | A61B 1/00105 |
| 9,835,821 B1* | 12/2017 | Yin | A61B 1/00163 |
| 9,965,856 B2* | 5/2018 | Weiss | H04N 5/2253 |
| 10,084,944 B2* | 9/2018 | Henley | H04N 5/2253 |
| 10,136,954 B2* | 11/2018 | Johnson | A61B 34/30 |
| 10,188,411 B2* | 1/2019 | Bonneau | A61B 17/221 |
| 10,219,864 B2* | 3/2019 | Bonneau | A61B 18/245 |
| 10,231,791 B2* | 3/2019 | LeBoeuf, II | A61B 5/064 |
| 2001/0017649 A1 | 8/2001 | Yaron | |
| 2001/0033326 A1 | 10/2001 | Goldstein et al. | |
| 2002/0021354 A1 | 2/2002 | Suzuki et al. | |
| 2002/0072653 A1 | 6/2002 | Ishizuka | |
| 2002/0154215 A1 | 10/2002 | Schechterman et al. | |
| 2003/0125608 A1 | 7/2003 | Igarashi | |
| 2003/0215608 A1 | 11/2003 | Bermel | |
| 2003/0233024 A1 | 12/2003 | Ando | |
| 2004/0082833 A1 | 4/2004 | Adler et al. | |
| 2005/0023356 A1 | 2/2005 | Wiklof et al. | |
| 2005/0267328 A1 | 12/2005 | Blumzvig et al. | |
| 2006/0025655 A1 | 2/2006 | Uram | |
| 2006/0076472 A1 | 4/2006 | Dosluoglu et al. | |
| 2006/0178559 A1* | 8/2006 | Kumar | A61B 34/37 600/109 |
| 2006/0183976 A1 | 8/2006 | Adler et al. | |
| 2007/0156285 A1* | 7/2007 | Sillman | G16H 40/40 700/245 |
| 2007/0232860 A1 | 10/2007 | Kubo et al. | |
| 2008/0065105 A1 | 3/2008 | Larkin et al. | |
| 2008/0185603 A1* | 8/2008 | Itoi | A61B 1/05 257/98 |
| 2008/0208006 A1 | 8/2008 | Farr | |
| 2008/0287963 A1* | 11/2008 | Rogers | A61B 1/00039 606/130 |
| 2008/0300463 A1 | 12/2008 | Navok et al. | |
| 2009/0096865 A1 | 4/2009 | McKinley | |
| 2009/0245600 A1 | 10/2009 | Hoffman et al. | |
| 2009/0248036 A1 | 10/2009 | Hoffman et al. | |
| 2010/0168918 A1* | 7/2010 | Zhao | B25J 9/1689 700/259 |
| 2010/0169815 A1* | 7/2010 | Zhao | B25J 9/1633 715/771 |
| 2010/0261961 A1* | 10/2010 | Scott | A61B 1/00193 600/111 |
| 2010/0317965 A1* | 12/2010 | Itkowitz | A61B 34/37 600/425 |
| 2010/0318099 A1* | 12/2010 | Itkowitz | A61B 34/30 606/130 |
| 2010/0331855 A1* | 12/2010 | Zhao | A61B 34/30 606/130 |
| 2011/0009880 A1 | 1/2011 | Prisco et al. | |
| 2011/0034769 A1 | 2/2011 | Adair et al. | |
| 2011/0043612 A1 | 2/2011 | Keller et al. | |
| 2011/0071347 A1* | 3/2011 | Rogers | A61B 1/00149 600/104 |
| 2011/0071541 A1* | 3/2011 | Prisco | A61B 17/3421 606/130 |
| 2011/0071543 A1* | 3/2011 | Prisco | A61B 17/0218 606/130 |
| 2011/0071544 A1* | 3/2011 | Steger | A61M 25/0105 606/130 |
| 2011/0115882 A1* | 5/2011 | Shahinian | A61B 1/00193 348/45 |
| 2012/0209288 A1* | 8/2012 | Robinson | A61B 34/30 606/130 |
| 2013/0250061 A1 | 9/2013 | Hofer | |
| 2014/0236177 A1* | 8/2014 | Verner | A61B 17/3462 606/130 |
| 2014/0253684 A1* | 9/2014 | Kumar | A61B 1/00009 348/45 |
| 2014/0336460 A1 | 11/2014 | Shafer et al. | |
| 2014/0343569 A1* | 11/2014 | Turner | A61B 17/28 606/130 |
| 2016/0166339 A1* | 6/2016 | Labonville | A61B 34/30 606/130 |
| 2017/0000575 A1* | 1/2017 | Griffiths | A61B 34/25 |
| 2017/0172394 A1 | 6/2017 | Scott et al. | |
| 2017/0172675 A1* | 6/2017 | Jarc | A61B 90/361 |
| 2017/0180720 A1* | 6/2017 | Jarc | H04N 13/383 |
| 2018/0206925 A1* | 7/2018 | Radel | A61B 34/37 |
| 2019/0216554 A1* | 7/2019 | Kapadia | A61B 34/30 |

FOREIGN PATENT DOCUMENTS

| | | | | |
|---|---|---|---|---|
| WO | WO-2014144947 A1 * | 9/2014 | | G06T 3/4007 |
| WO | WO-2014144986 A1 * | 9/2014 | | A61B 1/00006 |

(56) References Cited

FOREIGN PATENT DOCUMENTS

| WO | WO-2015126466 A1 | * | 8/2015 | ............ A61B 19/00 |
| WO | WO-2015163942 A1 | * | 10/2015 | ............ A61B 17/22 |

OTHER PUBLICATIONS

Y. Horise et al., Development of a locally-oprerated master device and a flexible slave robot system fo single-incision laparoscopic surgery, Int J CARS (Suppl 1), 2014, pp. 141-163 (Year: 2014).*

Marc O. Schurr et al, RObotics and systems technology for advanced endoscopic procedures: experiences in general surgery, Elsevier, 1999, 9 pgs (Year: 1999).*

Pandiscio, Mark, J. ,WO2013059821, ISR—Steerable Electronic Stereoscopic Endoscope, Apr. 25, 2013, 4 pgs (Year: 2013).*

Pandiscio, Mark, J. ,WO2013059821, Written Opinion—Steerable Electronic Stereoscopic Endoscope, Mar. 14, 2013, 6 pgs (Year: 2013).*

Blyth, Peter, "Converters Address Medical Equipment Compliance," Power Electronics Technology, Mar. 2006, pp. 38-41; Internet: www.powerelectronics.com.

PCT/US07/85714 International Search Report and Written Opinion of the International Searching Authority, dated Jul. 2, 2008, 10 pages.

Powervar, Inc., "IEC 601: What Are the Implications for Power Quality" White Paper # 211, 2002, 10 pages.

Sidebottom, Charles et al., IEC 60601-1, Third Edition, The Journal of Medical Device Regulation, May 2006, pp. 8-17.

Techneglas, Inc., "Frit Facts: A Brief Technological Summary of Television Solder Glass for CRT Technicians, Engineers and Managers," posted online Mar. 25, 2006, 40 pages, Internet: http://www.techneglas.com/products/frit.pdf.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wang L., et al., "Miniaturized, CMOS Imaging Module with Real-time DSP Technology for Endoscope and Laryngoscope Applications," Journal of Signal Processing Systems, 2009, vol. 54 (1-3), pp. 7-13.

\* cited by examiner

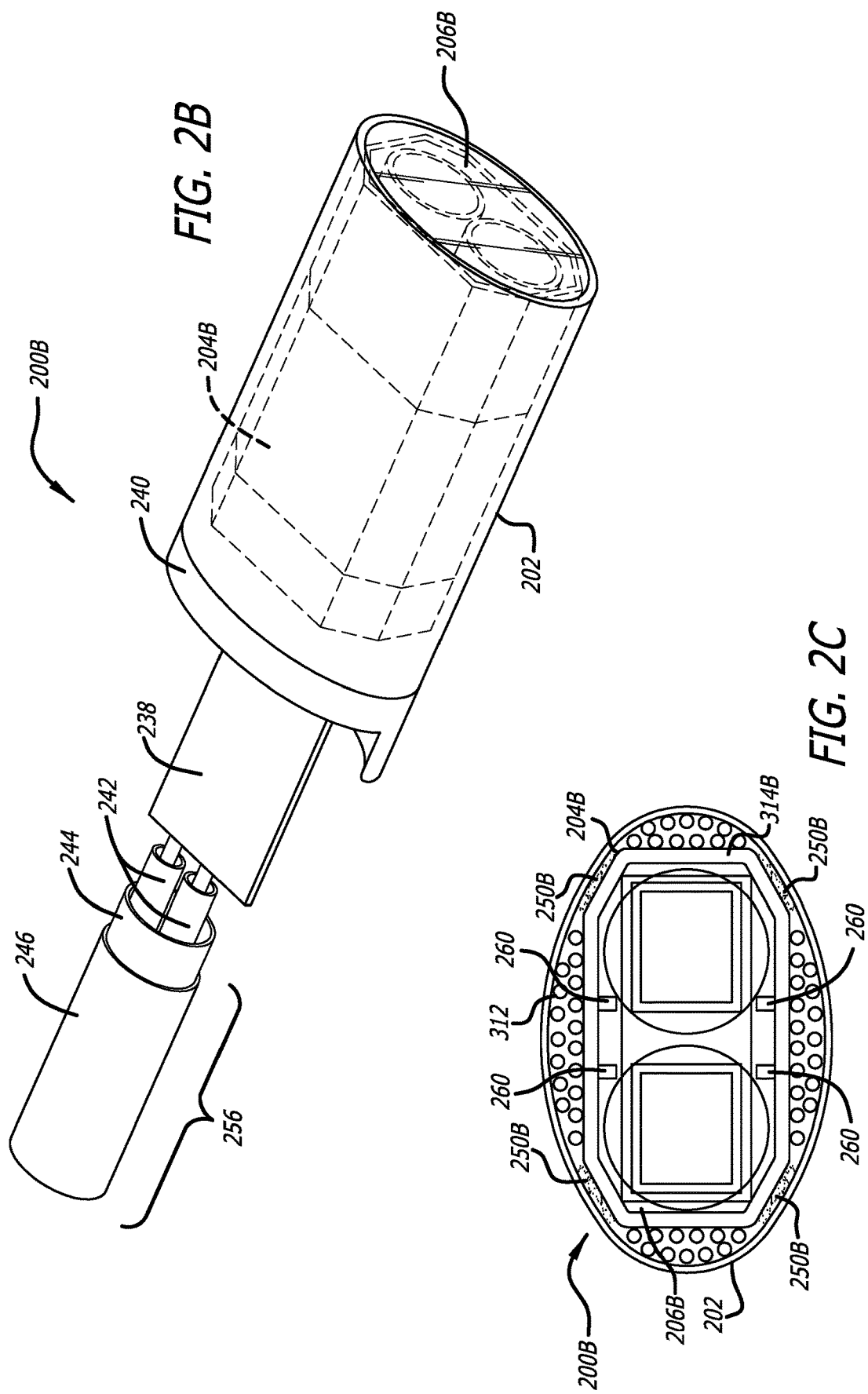

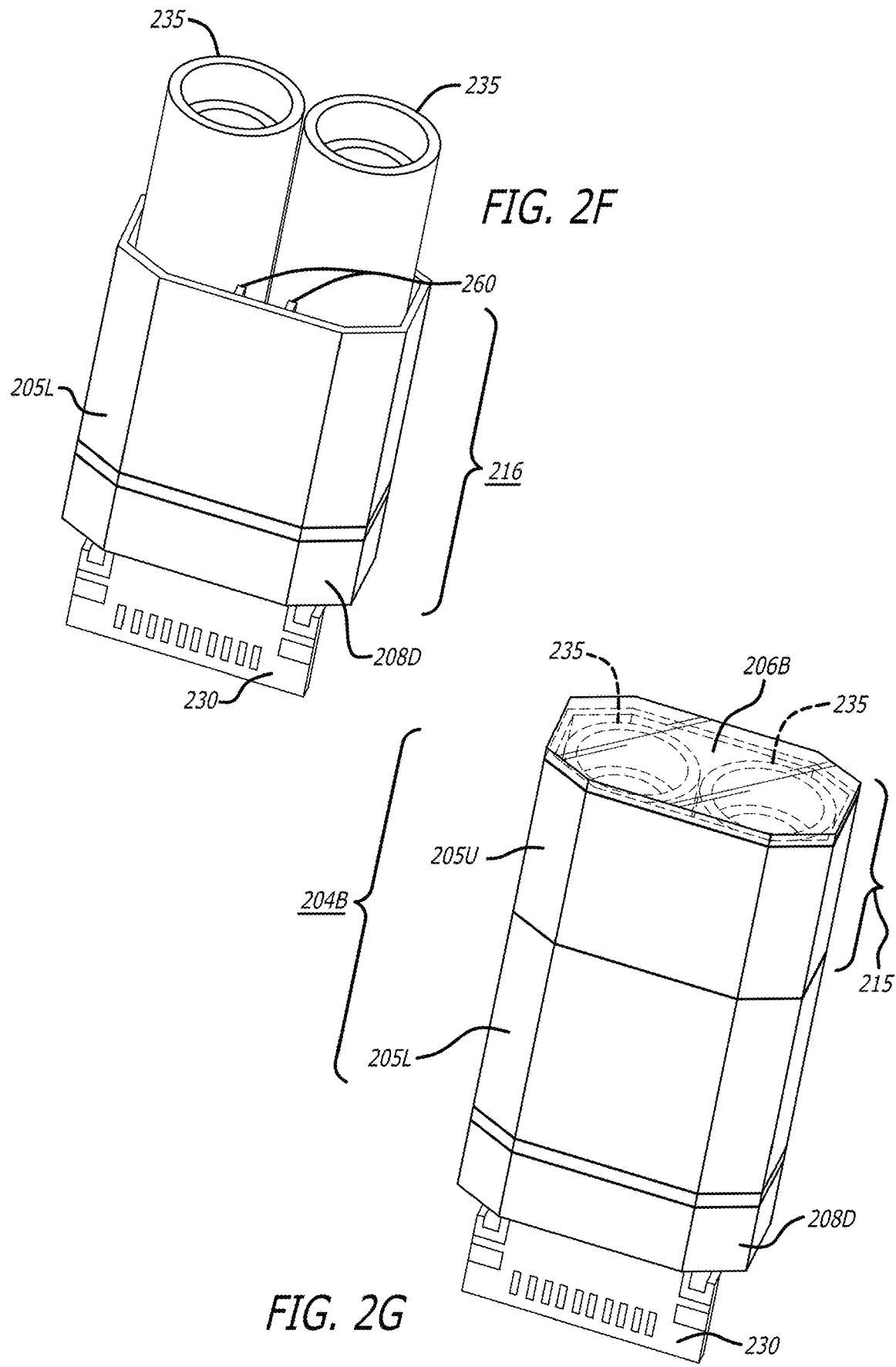

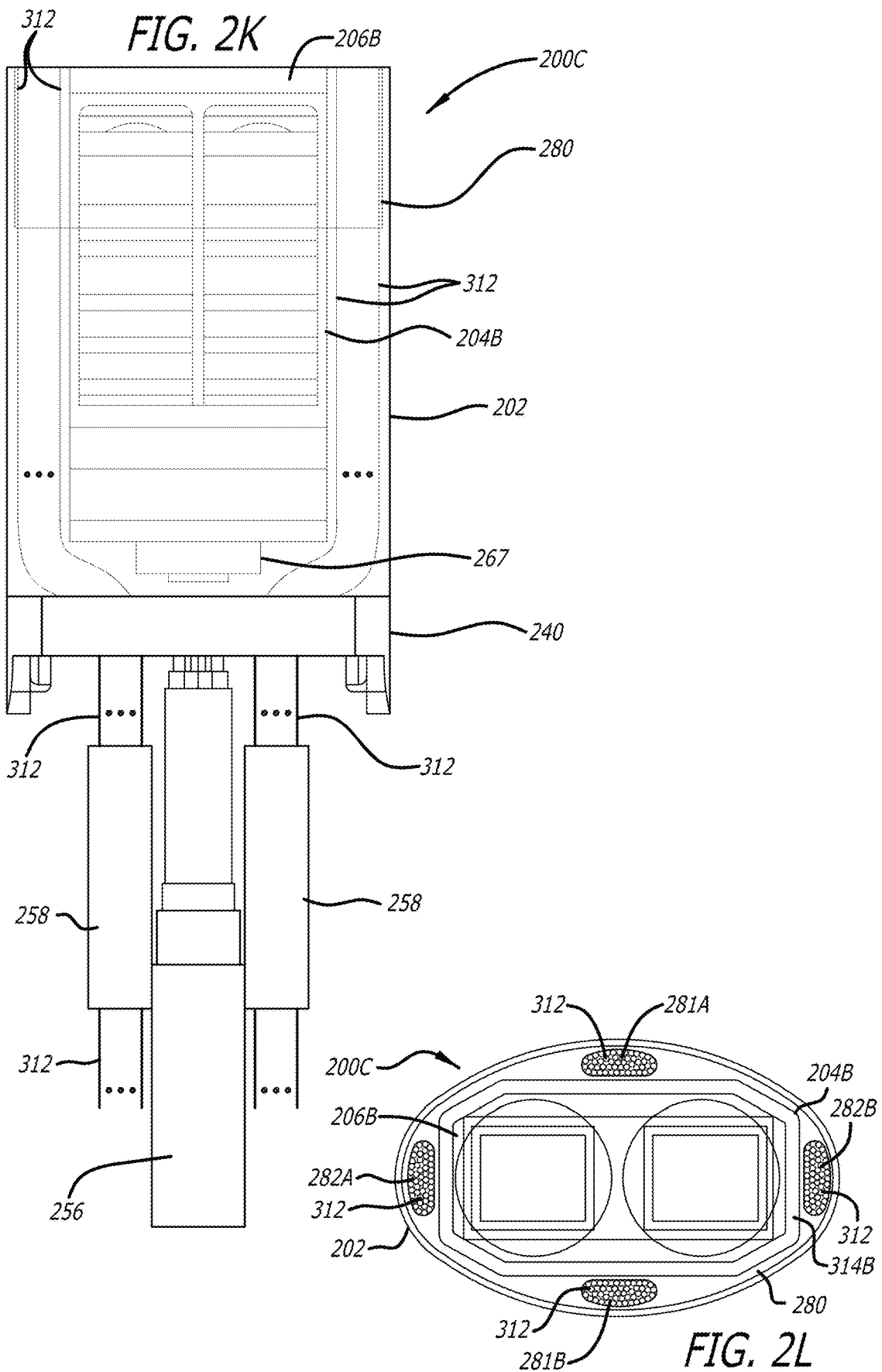

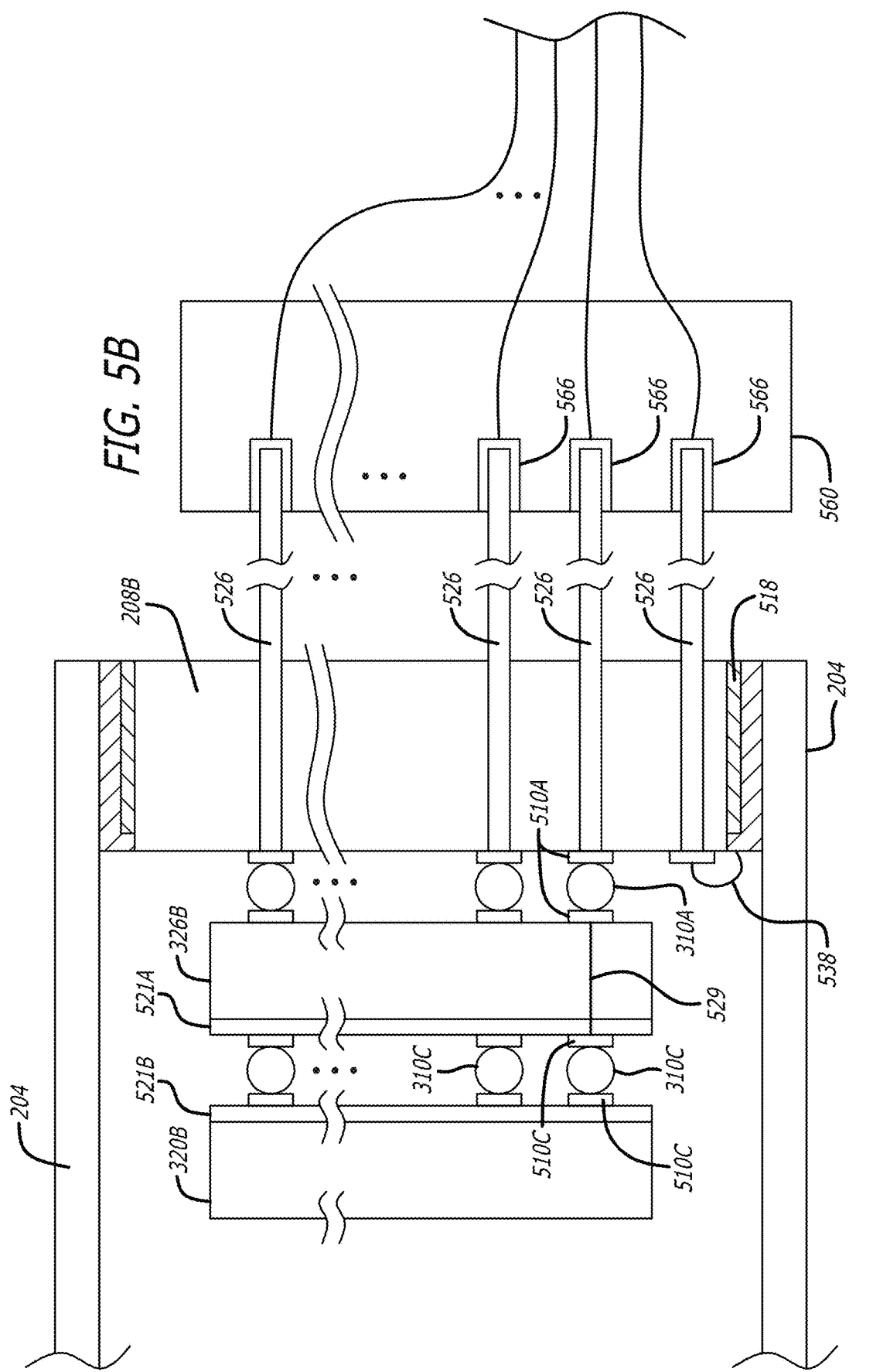

__US 10,682,046 B2__

SURGICAL SYSTEM WITH HERMETICALLY SEALED ENDOSCOPE

CROSS REFERENCE TO RELATED APPLICATIONS

This United States (U.S.) patent application claims the benefit and is a continuation of U.S. patent application Ser. No. 15/394,703 filed on Dec. 29, 2016 by David D. Scott et al., entitled ENDOSCOPE WITH DISTAL HERMETICALLY SEALED SENSOR, now allowed. U.S. patent application Ser. No. 15/394,703 claims the benefit and is a continuation of U.S. patent application Ser. No. 15/018,867 filed on Feb. 9, 2016 by David D. Scott et al., entitled, HERMETICALLY SEALED ENDOSCOPE WITH OPTICAL COMPONENT ATTACHED TO INNER PROTECTIVE WINDOW, issued as U.S. Pat. No. 9,565,997. U.S. patent application Ser. No. 15/018,867 claims the benefit and is a continuation of U.S. patent application Ser. No. 14/662,083 filed on Mar. 18, 2015 by David D. Scott et al., entitled, STEREO CAMERA FOR HERMETICALLY SEALED ENDOSCOPE, issued as U.S. Pat. No. 9,271,633. U.S. patent application Ser. No. 14/662,083 claims the benefit and is a continuation of U.S. patent application Ser. No. 14/030,122 filed on Sep. 18, 2013 by David D. Scott et al., entitled, HERMETICALLY SEALED ENDOSCOPE, issued as U.S. Pat. No. 9,005,113. U.S. patent application Ser. No. 14/030,122 claims the benefit and is a continuation of U.S. patent application Ser. No. 12/780,898 filed on May 15, 2010 by David D. Scott et al., entitled HERMETICALLY SEALED DISTAL SENSOR ENDOSCOPE, issued as U.S. Pat. No. 8,556,807. U.S. patent application Ser. No. 12/780,898 is a non-provisional application that claims the benefit and is a continuation-in-part of U.S. patent application Ser. No. 11/614,661 filed on Dec. 21, 2006 by inventors David C. Shafer, et al., entitled STEREOSCOPIC ENDOSCOPE, issued as U.S. Pat. No. 8,814,779, which is incorporated herein by reference.

FIELD

Aspects of the embodiments generally relate to minimally invasive surgical systems.

BACKGROUND

Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. The endoscopic surgical instruments generally include an endoscope (for viewing the surgical field) and working tools. In endoscopic surgery, the working tools are similar to those used in conventional (open) surgery, except that the working end or end effector of each tool is separated from its handle by an extension tube. As used herein, the term end effector means the actual working part of the surgical instrument and can include clamps, graspers, scissors, staplers, and needle holders, for example.

To perform endoscopic surgical procedures, the surgeon passes these working tools or instruments through the cannula sleeves to an internal surgical site and manipulates them from outside the abdomen. The surgeon may monitor the procedure within the internal surgical site by means of an endoscope, also referred to herein an endoscopic camera. Minimally invasive surgeries where an endoscopic camera is used are well known (e.g., arthroscopy, retroperitoneoscopy, pelviscopy, nephroscopy, cystoscopy, cisternoscopy, sinoscopy, hysteroscopy, urethroscopy and the like).

After each surgery, federal and state health regulations require that surgical tools be treated to prevent infection. Surgical tools that are to be reused are often cleaned, disinfected, and then sterilized after use in a prior surgery. Surgical tools may be cleaned with water, an enzymatic cleanser, and a scrub brush. Common methods of disinfecting surgical tools involves bathing them in a chemical disinfectant so that the surgical tool can be passed around within a hospital with a low level risk of infection. However, after being disinfected, a surgical tool shouldn't be used for surgery as not all bacterial has been killed. A surgical tool that is to be reused in another surgery should undergo a further sterilization process where all bacterial are killed so that the tool can be used again for surgery without transmitting bacteria from one patient to another. The sterilization process involves either a chemical sterilization using chemical sterilization techniques or a steam sterilization process using an autoclave.

Disinfection and sterilization by immersion in a chemical liquid may not be as environmentally friendly. Disposal of the used chemical is costly and may cause harm to the environment. Another drawback is that the chemicals are generally corrosive. Furthermore, chemical disinfection and sterilization may be slower than other methods. Thus, a surgical instrument may have greater lag time between surgeries.

Similarly, disinfection and sterilization using chemical gases such as ethylene oxide also have their drawbacks. Such gases are highly toxic and/or flammable. Extreme care must be used during and after the disinfection and sterilization process to ensure the safety of both the patient and medical staff. Disinfection and sterilization using gases may be complicated. A surgical instrument may have greater lag time between surgeries.

Almost all medical facilities have an autoclave and prefer to use steam sterilization of surgical instruments when they can. Commonly known as autoclave sterilization, this method of sterilization rapidly and effectively sterilizes surgical instruments without toxic chemicals and lengthy procedures. Autoclaving standards vary but two common standards require 134 degrees centigrade (C) at 2 atmospheres for 3 minutes (U.S. Standard) and 134 degrees Celsius at 2 Atmospheres for 18 minutes (European Standard). Autoclaving requires less time than other disinfection methods and does not require the use of toxic chemicals. However, some surgical instruments can't tolerate the heat and moisture from steam sterilization in an autoclave.

The steam from autoclaving may cause conventional endoscopes to fail. Pressurized steam may damage the adhesives, optics, electronics, focusing mechanisms, and opto-electronics (e.g., image capturing circuit). Moisture in the endoscope may also condense on a lens and blur images. The adhesive mount for the lens of an endoscope may be adversely affected by the heat and moisture of an autoclave. A stereoscopic lens system is especially susceptible to autoclave damage, because the relative alignment of the right and left lenses (optical paths) is important to rendering depth in the stereo image. Heat deformation of a lens mount due to thermal expansion effects may alter the relative alignment of the stereoscopic lenses.

BRIEF SUMMARY

Certain aspects of the embodiments are summarized by the claims.

BRIEF DESCRIPTION OF THE DRAWING

FIG. 2B is a perspective view of an embodiment of a cylindrical shaped camera module with a polygonal inner housing.

FIG. 2C is a top view of a cylindrical shaped camera module with polygonal inner housing.

FIG. 2F is a perspective view of an embodiment of a cylindrical shaped camera module with polygonal inner housing with cap assembly removed.

FIG. 2G is a perspective view of an embodiment of a cylindrical shaped camera module with polygonal inner housing with cap assembly attached.

FIG. 2K is a side view of the assembled cylindrical shaped camera module shown in FIG. 2J.

FIG. 2L is a top view of the assembled cylindrical shaped camera module shown in FIGS. 2J-2K.

FIG. 5B is a magnified side schematic view of an alternate embodiment of a camera module.

Figure 1A:
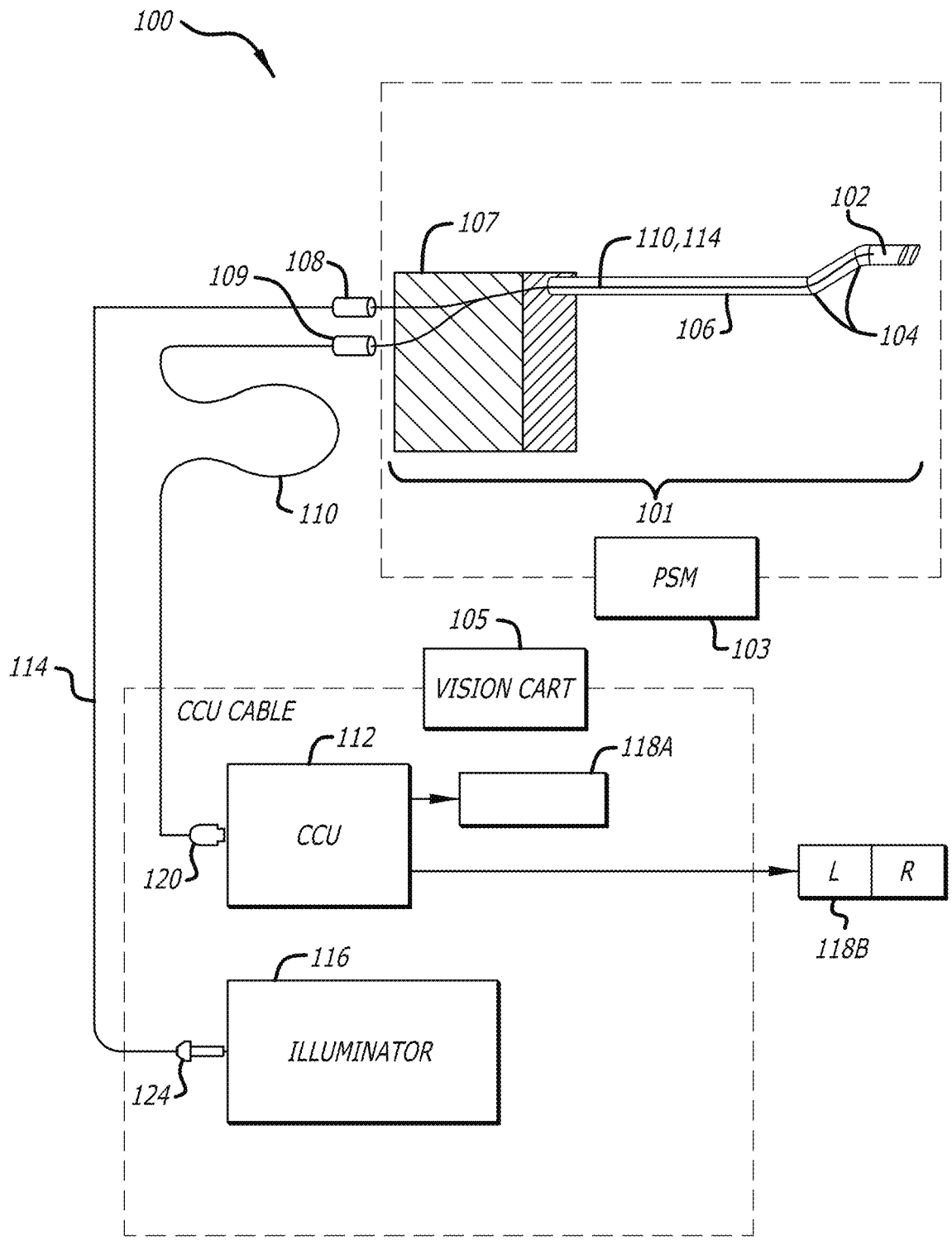
FIG. 1A is a system diagram showing the various components of an endoscopic camera system for use in robotic surgery.

Like reference numbers and designations in the drawings indicate like elements providing similar functionality. The figures are not drawn to scale so that elements, features, and surface structure may be shown by example and are intended merely to be illustrative and non-limiting of the aspects of the embodiments that are claimed.

DETAILED DESCRIPTION

This detailed description describes exemplary implementations that are illustrative of aspects of the embodiments, and so it is explanatory and not limiting. The claims define inventive aspects. In the drawings, some elements have been omitted to more clearly show inventive aspects.

Introduction

A robotic surgical system allows the surgeon to see and operate inside a patient's body without opening up the entire body cavity. Robotic surgical arms perform the surgery through small entry ports in the patient's body. These surgical arms are controlled by a surgeon at a surgeon's console control station. A video image of the surgical site may be captured by an imaging device attached to a robotic appendage and inserted into the surgical site. Video monitors at the surgeon's console display the video image of the surgical site. Using a real time display the surgeon coordinates the movement of the robotic arms and manipulates the attached surgical tool or end effectors.

Surgical tools, including imaging device, surgical scissors, graspers, or laser cutters, etc, are connected to a wristed joint capable of multiple degrees of freedom of movement. The wristed joint may use disks or vertebrae and actuation cables or tendons to allow a surgeon to remotely manipulate the end effector within small tight enclosures with a high degree of precision from a master control workstation or console. An exemplary wristed joint is described in detail in U.S. Pat. No. 6,817,974 entitled SURGICAL TOOL HAVING POSITIVELY POSITIONABLE TENDON-ACTUATED MULTI-DISK WRIST JOINT filed by Thomas G. Cooper et al. on Jun. 28, 2002 which is incorporated herein by reference.

An image device described as one embodiment is a video camera to capture video images of the surgical site. A video camera may capture images in the visible and near infrared (NIR) spectrum and uses one or more light sources in the visible and near infrared to illuminate the tissue surface in a surgical site. A digital video camera with a charge-coupled device (CCD) or complementary metal oxide semiconductor (CMOS) sensor may be used to capture digital video images of a surgical site. A bundle of optical fibers, connected at one end to a light source, may be used as light pipes to direct light down into the surgical site and provide the illumination to capture the digital video images. The video images captured by the camera may be transmitted to one or more viewing monitors that a surgeon uses to visualize the internal anatomy and guide any surgical procedures. The video images can be captured and displayed monoscopically by using a non-stereo camera and a single display device, or captured and displayed stereoscopically by using a stereo camera and a stereo display device.

Further information regarding robotic surgical systems may be found, for example, in U.S. patent application Ser. No. 11/762,165, entitled MINIMALLY INVASIVE SURGICAL SYSTEM, filed by David Q. Larkin et al. on Jun. 13, 2007 (U.S. Pat. No. 9,060,678); and U.S. Pat. No. 6,331,181, entitled SURGICAL ROBOTIC TOOLS, DATA ARCHITECTURE, AND USE, filed by Tierney et al on Oct. 15, 1999, both of which are incorporated herein by reference.

Distal Sensor Endoscope System Overview

To perform the precise movements necessary in endoscopic and laparoscopic surgery, it is imperative that the surgeon has a clear unobstructed view of a surgical site.

FIG. 1A is a block diagram illustrating a schematic representation of an endoscope camera system 100. The endoscope camera system 100 is a part of a robotic surgical system for viewing the surgical site within a patient. The endoscope camera system 100 includes an endoscopic camera instrument 101, a camera control unit (CCU) 112, and an illuminator 116 coupled together as shown.

The endoscopic camera instrument 101 comprises a camera module 102, a hollow instrument shaft 106, an instrument housing 107, and cables 110,114 coupled together as shown. The instrument housing 107 includes an interface base configured to mount to and dismount from a robotic arm. The instrument housing may have an electrical connector (not shown) to couple to an electrical connector of the robotic arm to communicate control signals. The camera module 102 may be coupled to the distal end of a joint of one or more joints 104 of the instrument so that it is capable of one or more degrees of freedom of movement. One or more of the joints 104 may be a wristed joint coupled to an end or considered to be a part of the instrument shaft 106. One or more of the joints 104 may be joggle joints with a joggle links there between. The instrument shaft 106 is relatively long and thin so as to pass through a cannula sleeve in an entry port of a patient into an internal surgical site. Alternatively, the instrument shaft 106, joints 104, and camera module 104 of the instrument 101 are inserted into an entry guide that is passed through the cannula sleeve into the body. A proximal end of the instrument shaft 106 is coupled to the instrument housing 107. The instrument housing 107 houses the mechanisms (not shown) to manipulate cables to move the joints 104 and the camera module 102 within a surgical site under control of the operating surgeon.

The camera instrument 101 is coupled to a robotic arm of a Patient Side Manipulator (PSM) 103 under the control of the operating surgeon that may move the shaft 106, the joints 104 and the camera module 102 within the surgical site. The wristed joints 104 allow articulation inside the patient body cavity with minimal movement of the instrument shaft 106. For example, the wristed joint 104 may allow a surgeon to move the camera module to view an organ from multiple angles, while the instrument shaft 106 remains stationary. The wristed joints 104 are articulated by a plurality of cables nested within the wrist joint and extending back through the instrument shaft 106 into the instrument housing 107. Ends of the cables may be taken in or let out to articulate movement in a joint.

In one embodiment, the joint 104 nearer the midpoint of the shaft is a parallel motion mechanism, also referred to herein as a joggle joint. A parallel motion mechanism allows the position of a reference frame at the distal end of the mechanism to be changed with respect to a reference frame at the proximal end of the mechanism without changing the orientation of the distal reference frame. A parallel motion mechanism (joggle joint) and a wristed joint (wrist mechanism) that may couple to an end effector, such as the camera instrument module 102, are further disclosed in U.S. patent application Ser. No. 11/762,165, entitled MINIMALLY INVASIVE SURGICAL SYSTEM, filed by Larkin et al. on Jun. 13, 2007 (U.S. Pat. No. 9,060,678) which is incorporated herein by reference.

Sheathed electrical cables 110 may detachably couple at one end to the camera control unit (CCU) 112 and run through the instrument housing 107, instrument shaft 106, and the wristed joint 104 to couple to the camera module 102. In one embodiment, the sheathed electrical cables 110 include electrical cables to allow the transmission of video signals from the camera module 102 to the CCU 112. In one embodiment, the sheathed electrical cables 110 also include an optical fiber to allow the transmission of video signals from the camera module 102 to the CCU 112. Control signals and power/ground may also be routed over electrical cables in the sheathed electrical cable 110 between the CCU 112 and the camera module 102. The control signals may be used to control the camera module 102, the capture of images in the surgical site, and the transmission of images to the CCU 112.

In FIG. 1A, video images in a video signal processed by CCU 112 from the camera module 102 may be displayed in stereo on a stereo viewer 118B or displayed on a monitor 118A mounted to a vision cart 105. In some embodiments, the CCU 112 and the illuminator 116 are also components mounted onto the vision cart 105. In other embodiments, the CCU 112 may be incorporated into a master control console where the surgeon may control the endoscopic camera system 100 or into the patient side manipulator 103.

A light guide 114 formed of one large optical fiber or a bundle of strands of optical fiber has a light guide connector 124 to couple to the illuminator 116 to receive light. The external illuminator 116 may include one or more of a Xenon short-arc lamps, a lasers, light emitting diodes (LEDs), and/or other types of light generators. The light guide directs the generated light out its distal end(s) out from the camera module 102 near an image sensor. With a plurality of strands of optical fiber, the light guide 114 can terminate at more than one point at the distal end of the camera module 102 and provide multiple light points. As further detailed below, individual threads or strands of optical fibers may be placed in a mold and bonded with epoxy to create shaped light emitters. The fiber optic cables may be bundled together and sheathed so that they may be routed through the center of the instrument shaft 106 and the one or more joints 104 to the camera module 102.

Alternatively to illuminate a surgical site with light, one or more LEDs may be included as part of the camera module 102, space permitting, instead of employing the light guide 114 and its fiber optic cables coupled to the external illuminator 116.

Sterilization and safety regulations require that surgical tools including endoscopic camera instruments 101 are sterilized prior to each surgery. The modular instrument housing 107 and quick disconnect cables 110,114 allow the endoscope system 100 to be quickly detached and used in another surgery. The light guide cable 114 and/or the sheathed electrical cables 110 may further include intermediate connectors 109,108 respectively to further facilitate a quick disconnect for sterilization. An autoclave can sterilize an instrument in minutes, but the surgical instrument must be capable of withstanding the intense heat, moisture, and pressure of an autoclave. The delicate sensors of an endoscope are especially susceptible to the steam cleaning process of an autoclave. By hermetically sealing the delicate optical components of an endoscope, without organic adhesives, an autoclaveable surgical tool may be achieved.

Figure 1B:
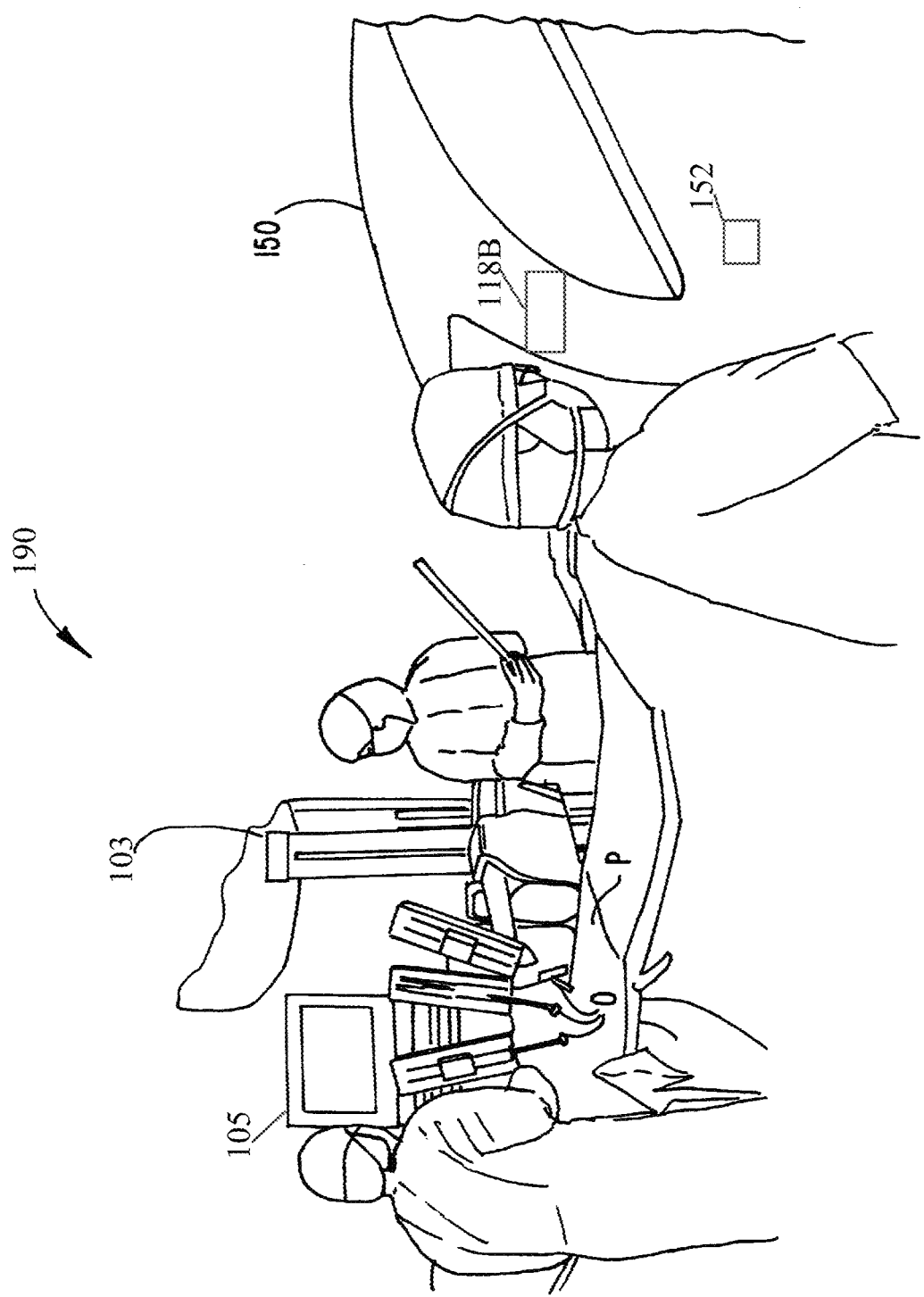
FIG. 1B is a system diagram illustrating various components of a minimally invasive surgical system with the endoscopic camera system of FIG. 1A.

Referring now to FIG. 1B, the minimally invasive surgical system 190 generally includes the master control console or workstation 150, the patient side manipulator 103, and the vision cart 105 coupled in communication together. The master control console 150 generally includes master controllers (not shown) which are grasped by the surgeon and manipulated in space while the surgeon views the procedure on the stereo display 118B. The master controllers are manual input devices which preferably move with six degrees of freedom, and which often further have an actuatable handle for actuating tools (for example, for closing grasping jaws, applying an electrical potential to an electrode, or the like). The master control console 150 includes at least one processor 152 to control the system 190.

The patient side manipulator 103 is positioned adjacent to the body of a patient P and moves tools, such as the camera instrument 101, that have shafts. The shafts extend into an internal surgical site within the patient body via openings O. As illustrated in FIG. 1B, one or more assistant may be present during surgery to assist the surgeon, particularly during removal and replacement of tools. The patient side manipulator 103 includes a base from which surgical tools, including the camera instrument 101, are supported. More specifically, the surgical tools are each supported by a series of manually articulatable linkages, generally referred to as set-up joints, and a robotic arm or manipulator.

Cylindrical Endoscopic Camera Module

One embodiment of a hermetically sealed distal sensor endoscope may be achieved by forming the camera module 102 within a moisture resistant cylindrical structure so the camera module is autocleaveable. A first hollow moisture resistant housing (inner housing) encloses optical components such as lenses and image sensors. Optical fibers of the light guide are arranged around the first housing. A second hollow housing (outer housing) encloses the optical fibers, the first housing, and the optical components.

Figure 2A:
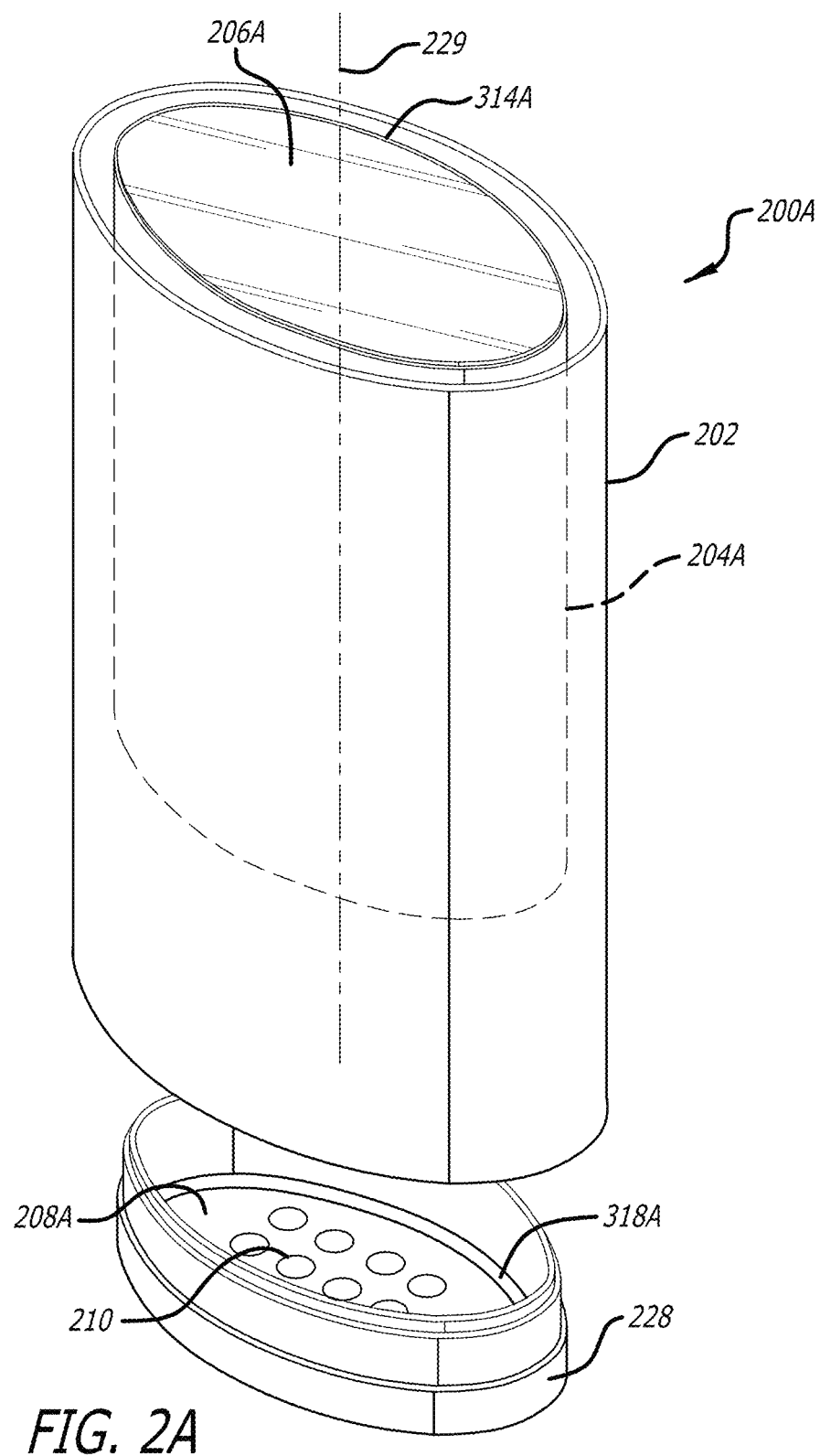
FIG. 2A is an exploded perspective view of portions of an embodiment of a cylindrical shaped camera module.

Referring now to FIG. 2A, a perspective view of a double walled cylindrical structure 200A with a moisture resistant inner housing is shown that may be used to house the electrical, optical, and electro-optical components of the camera module 102. The double walled cylindrical structure 200A includes an outer hollow cylindrical housing (may also be referred to as an outer can or outer housing) 202 and an inner hollow cylindrical housing (may also be referred to as an inner can or inner housing) 204A that is coaxial with the outer hollow cylindrical housing 202 along an axis 229. The double walled cylindrical structure 200A further includes a window 206A hermetically sealed to the distal end of the inner housing 204A with a hermetic sealant forming a first hermetic seal 314A. A substrate 208A hermetically sealed to the proximal end of the inner housing 204A with a second hermetic sealant forms a second hermetic seal 318A. The ceramic substrate 208A, shown detached from the inner housing 204A in FIG. 2A, acts as a hermetic barrier.

The inner housing 204A and the outer housing 202 may be made of stainless steel, titanium, another metal or metal alloy (e.g., KOVAR, a nickel-cobalt ferrous alloy) sufficiently strong and light enough to be used in surgical instruments. The material chosen to form the inner housing 204A and the outer housing 202 should be able to withstand the heat and moisture of an autoclave as well as the oxidizing conditions found in most surgical sites. Another consideration when selecting the material to form the inner housing 204A is thermal expansion. The inner housing 204A is welded to ceramic substrate 208A. If the materials each expand at a different rate while welded together, stress fractures may develop in the ceramic or the welds. In order to reduce stress on the ceramic substrate due to thermal expansion, it may be beneficial to form the inner housing out of a material, such as a nickel-cobalt ferrous alloy (KOVAR), which substantially matches the thermal expansion coefficient of the substrate (the substrate is a high temperature co-fired multilayer ceramic in one embodiment) and a window (e.g., a sapphire window) so that hermetic seals between each survive a sterilization process in an autoclave. In an alternate embodiment, the outer housing 202 is overmolded silicon formed by over molding silicon around the inner housing 204A, optical fibers 312, and the segment 240 into the shape of the outer housing 202.

Both the outer cylindrical housing 202 and the inner cylindrical housing may have a similar hollow shape but with different diameters and/or radiuses. In one embodiment, both the outer cylindrical housing 202 and the inner cylindrical housing 204A have a hollow oval or elliptical cross-section. Note that the term cylinder is used herein in a broad sense to not only encompass circular cylinders with a circular or oval cross section but all types of polygonal shaped cylinders with a polygon cross section that may alternatively be referred to as a prism.

Sandwiched in between the outer housing 202 and inner housing 204A are a plurality of optical fibers (not shown in FIG. 2A; see optical fibers 312 shown in FIG. 2C, for example). The optical fibers may be bundled into cables and routed to specific points at the top of the endoscopic camera 202 to provide light from discrete light points. For example, four bundles of optical fibers may be routed to the cardinal points at the distal end of the camera module 200B to produce light from four points around the camera lens such as shown in FIG. 2C. Alternatively, the optical fibers may be placed continuously between outer housing 202 and inner housing 204A to provide a "halo" light source around the camera window. In both embodiments, the optical fibers are polished at the distal end flush with the outer housing 202 edge to provide a smooth top surface, which prevents the intrusion of biological matter and is easier to clean. If the optical fibers are routed to specific points, then a sealant or potting material (e.g., silicon epoxy) may be placed between the outer housing 202 and inner housing 204A to provide a barrier. As previously mentioned, the optical fibers may be gathered near the base of the camera module 102 and routed down the central axis of the wristed joint and instrument shaft to connect to an external illuminator 116. A sheath may be used to protect the optical fiber bundles as they extend down the length of the endoscopic camera instrument 101.

Optical components for focusing incoming light and capturing images are hermetically sealed within the inner housing 204A to avoid moisture during steam sterilization in an autoclave. The inner housing 204A may also be grounded to form a Faraday cage and shield internal components from electrical noise. To hermetically seal the inner housing 204A, a ceramic substrate (a base) 208A and a window (a lid) 206A are attached to open ends of the inner housing 204A. A first hermetic seal 314A is created by soldering the perimeter of the window (lid) 206A to the inside edge of the distal end of the inner housing 204A. A second hermetic seal 318A is created by welding the perimeter of the ceramic substrate (base) 208A to the inside edge of the proximal end of the inner housing 204A.

In FIG. 2A, a portion of camera module 200A is detached from the bottom of inner housing 204A. The ceramic substrate (base) 208A is shown hermetically sealed to a ring 228. The ring 228 in turn is coupled to the inner housing 204A. The substrate (base) 208A may be made of a high-temperature co-fired multilayer ceramic substrate. The ring 228 may be a metal ring (e.g., a nickel-cobalt ferrous alloy such as KOVAR) that is welded to a metal inner housing. A first set of bond pads 210B (see pads 210B in FIG. 3A) are on the outer surface of ceramic substrate 208A and are electrically connected to a second set of bond pads 210A on the inside surface of ceramic substrate 208. Metallization of the outside edge of ceramic substrate 208A may improve welding of the ceramic substrate 208A to the ring 228. Alternatively, a ring of gold may be deposited on top of ceramic substrate 208A near the perimeter. Inner housing 204A may be placed atop the deposited gold and welded, brazed, or laser welded to the ceramic substrate 208A.

Polygonal Inner Housing

FIG. 2B is a perspective view of a camera module 200B with an inner housing 204B having a different shape than that of the inner housing 204A. While the inner housing 204B is still a hollow cylinder and coaxial with the outer housing 202, it has a polygonal-shaped cross section to provide greater interior volume that accommodates relatively larger optical and electrical components than a similarly sized cylinder with a curved cross section. In one embodiment, the inner housing has an octagon-shaped cross section. The cross section of the substrate and the ring (shown in FIGS. 2D and 2E) also matches the polygonal shape of the inner housing 204B as does the cross section of the window 206B shown in FIG. 2B. As better shown in FIG. 2G, the hollow polygonal shaped inner housing 204B includes an upper hollow polygonal shaped inner housing portion 205U and a lower hollow polygonal shaped inner housing portion 205L. An opening of the lower hollow polygonal shaped inner housing portion 205L is closed by the ceramic substrate (base) 208D. An opening of the upper hollow polygonal shaped inner housing portion 205U is closed by the polygonal shaped window 206B.

A top view of the camera module 200B, shown in FIG. 2C, illustrates the polygonal shaped window 206B coupled to the upper hollow polygonal shaped inner housing portion 205U of the inner housing 204B by a hermetic seal 314B conforming to the polygonal shape. A plurality of optical fibers 312 are positioned at points between the inner housing 204B and the outer housing 202. A dielectric epoxy 250B fills the gaps between the inner housing 204B, the optical fibers 312, and the outer housing 202.

Figure 2D:
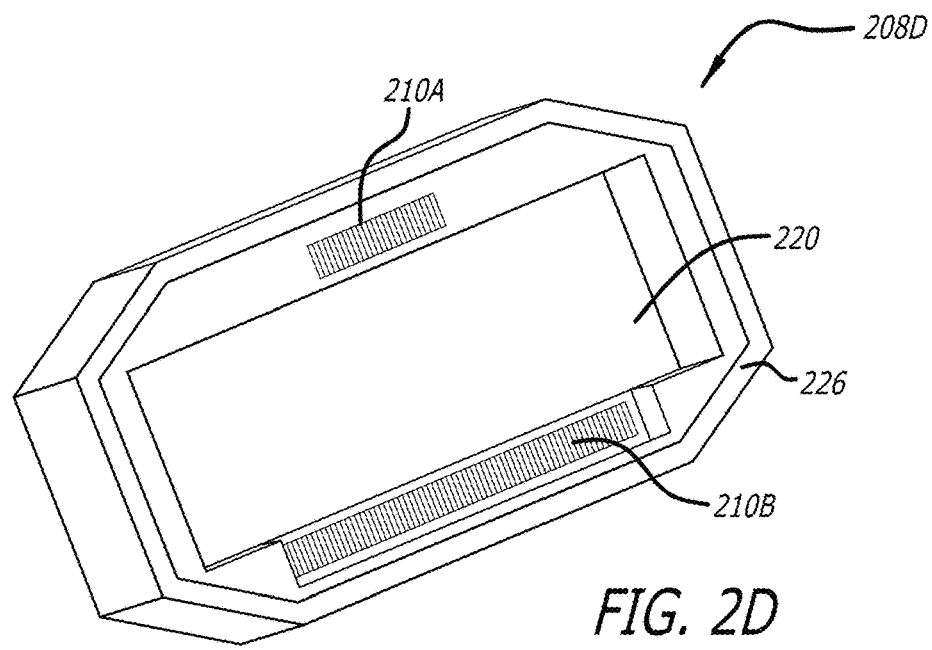
FIG. 2D is a top perspective view of a substrate.

FIG. 2D is a perspective view of the inner side of the polygonal substrate 208D. The inner side of the polygonal substrate 208D includes a cutout recess 220 to receive an image sensor and a processor (e.g., image sensor 320B and signal conditioning processor 326B shown in FIGS. 5B, 6A-6B). Above and below recess 220 are bond pads 210A and 210B for making electrical connections to the image sensor 320B and processor 326B. As mentioned previously, a layer of gold is deposited around the perimeter of the substrate to facilitate a metal to ceramic bond. A gold layer 226 deposited around the perimeter of the polygonal substrate 208D allows the lower portion 205U of the inner housing 204B to be welded or soldered onto the polygonal substrate 208D.

Figure 2E:
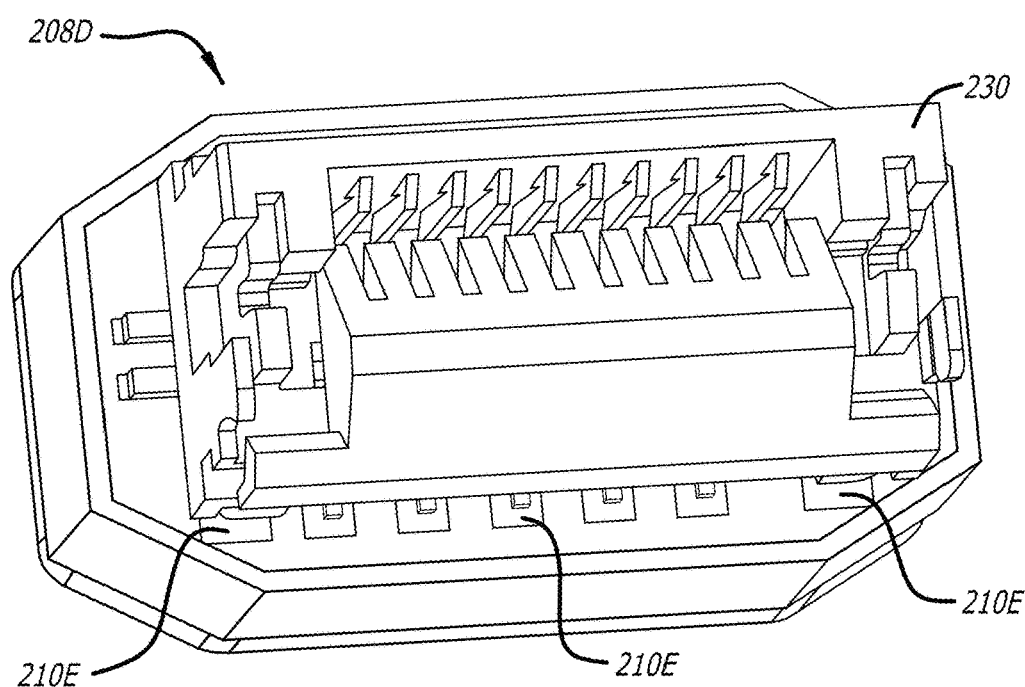
FIG. 2E is a back perspective view of a substrate with attached ribbon connector.

FIG. 2E shows a perspective view of an outer side or backside of the polygonal substrate 208D. On the backside of polygonal substrate 208D are multiple bond pads 210E. Bond pads 210E allow a ribbon connector 230 to be surface mounted to the bond pads on the back side of polygonal substrate 208D. The use of the ribbon connector 230 capable of receiving a ribbon cable can be advantageous for quick removal and replacement of the camera module 102. Although there are some advantages to using ribbon connector 230, other types of connectors may be substituted with similar results. Other means of transmitting data to and from a distal mounted endoscope are detailed below in the description of FIGS. 3A-5B.

FIGS. 2F-2G are perspective views illustrating assembly of the polygonal inner housing 204B. In FIG. 2F, a pair of lens barrels 235, also referred to as lens tubes, are placed within the lower portion of polygonal inner housing 204B separately aligned with respective pixel arrays of an image sensor as further described herein. Alternatively, the lenses and other optic devices may be held in a common lens holding structure that provides for alignment with the pixel arrays of the image sensor.

The lower and/or upper portions of the inner housing 204B provide a frame to hold the lens barrels. The pair of lens barrels 235 may be glued or laser welded to the lower and/or upper portions of the inner housing 204B. The pair of lens barrels 235 and the lower and/or upper portions of the inner housing 204B are designed to be thermally matched so that the lenses and other optic devices do not suffer misalignment during and after an autoclave sterilization process. Rails 260 may be mounted on the inside of polygonal inner housing 204B to help hold the lens barrels 235 aligned in place.

Lens barrels 235 may comprise a metallic tube to allow spot welding to rails 260. The lens barrel 235 may be formed out of a material with a similar coefficient of thermal expansion as the inner housing 204B to help reduce stress fractures. Lens barrels 235 hold the optics (e.g., one or more lenses) for focusing incident light onto the image sensor. A plurality of lenses are placed within the lens barrel 235 and separated by spacers. It is advantageous to form the lens barrel 235 without using adhesives due to the intense heat a camera module 200B will encounter in an autoclave. Melted glue may impair the focusing abilities of lens barrel 235 and blur the resulting image. However, heat-resistant glues may be used to glue optical components such as the lens barrel 235 to a transparent window.

In an alternative embodiment, inner housing 204B may be a solid cylindrical shape with tunnels bored out of the solid cylindrical shape to hold the lens barrels 235. In such an embodiment, the rails 260 may no longer be needed to hold the lens barrels in place.

Substrate 208D may be hermetically sealed to the bottom half 205U of inner housing 204B by soldering or welding to form a lower subassembly 216 of the inner housing. A ribbon connector 230 may be surface mounted to bond pads on the back side of substrate 208D for data transmission. The ribbon cable 238 has electrical wires that may couple to terminals of the ribbon connector 230.

For each camera module 200A-200B, the window (lid) 206A,206B is coupled to the distal end of the inner housing 204A,204B. The window 206A,206B may be made of any suitably scratch-, heat-, moisture-, and solvent-resistant material that is also transparent to a range of wavelengths of light detected by the image sensor behind the window. In one embodiment the window (lid) 206A,206B is a sapphire window brazed onto the inner wall or an edge of the upper housing portion 205U of the inner housing 204A,204B. To braze a sapphire window 206A,206B onto a metallic surface, the peripheral edge of the sapphire window may be metalized to aid adhesion. In other embodiments, the sapphire window 206A,206B may be gold soldered to the upper housing portion 205U of the inner housing 204A,204B using a gold solder to form the hermetic seal. In another embodiment, glass frit technology may be used to bond and seal the sapphire window to the inner housing. In this case, a glass frit sealant is used to form a glass frit seal about the sapphire window.

Once the lens barrels 235 are placed within inner housing 204A,204B and properly aligned with the image sensors, the inner housing 204A,204B is hermetically sealed. In one embodiment, an open end of a cap assembly 215 is placed over the lens barrels 235 and laser welded to the lower hollow housing portion 205L of the inner housing 204A, 204B. Cap assembly 215 includes the upper hollow housing portion 205U of the inner housing 204A,204B and the hermetically sealed window 206A,206B closing one end. With the cap assembly 215 laser welded to the lower inner housing portion 205L and the ceramic substrate hermetically sealed an end of the lower housing portion 205U, the inner housing 204A,204B is a hermetically sealed unitary piece. The use of a cap assembly 215 may aid in manufacturing, but other methods of assembling the hermetically sealed inner housing 204A,204B should be evident to those skilled in the art.

In one embodiment, the lower hollow housing portion 205L may be formed of a metal alloy (e.g., steel, iron, nickel, cobalt, and Gadolinium). The lens barrels 235 may be also be formed of a metal or an alloy. The upper housing portion 205U may be formed of a metal or alloy. The cap assembly 215 is inserted over the lens barrels near the lower hollow housing portion 205L and held in position to make a laser weld along the seam and form a third hermetic seal between the upper housing portion and the lower housing portion.

Dry nitrogen gas may be introduced within the inner housing 204A,204B to preserve the delicate circuitry and optics from oxidation. During the hermetic sealing process of the inner housing 204A,204B, dry nitrogen gas may be injected into the inner hollow chamber formed by the inner housing. Alternatively, the sealing process may be done in a nitrogen rich environment so that nitrogen gas is captured within the inner hollow chamber formed by the inner housing. The process of assembly may also be conducted in a "clean room" to further reduce manufacturing defects.

Figure 2H:
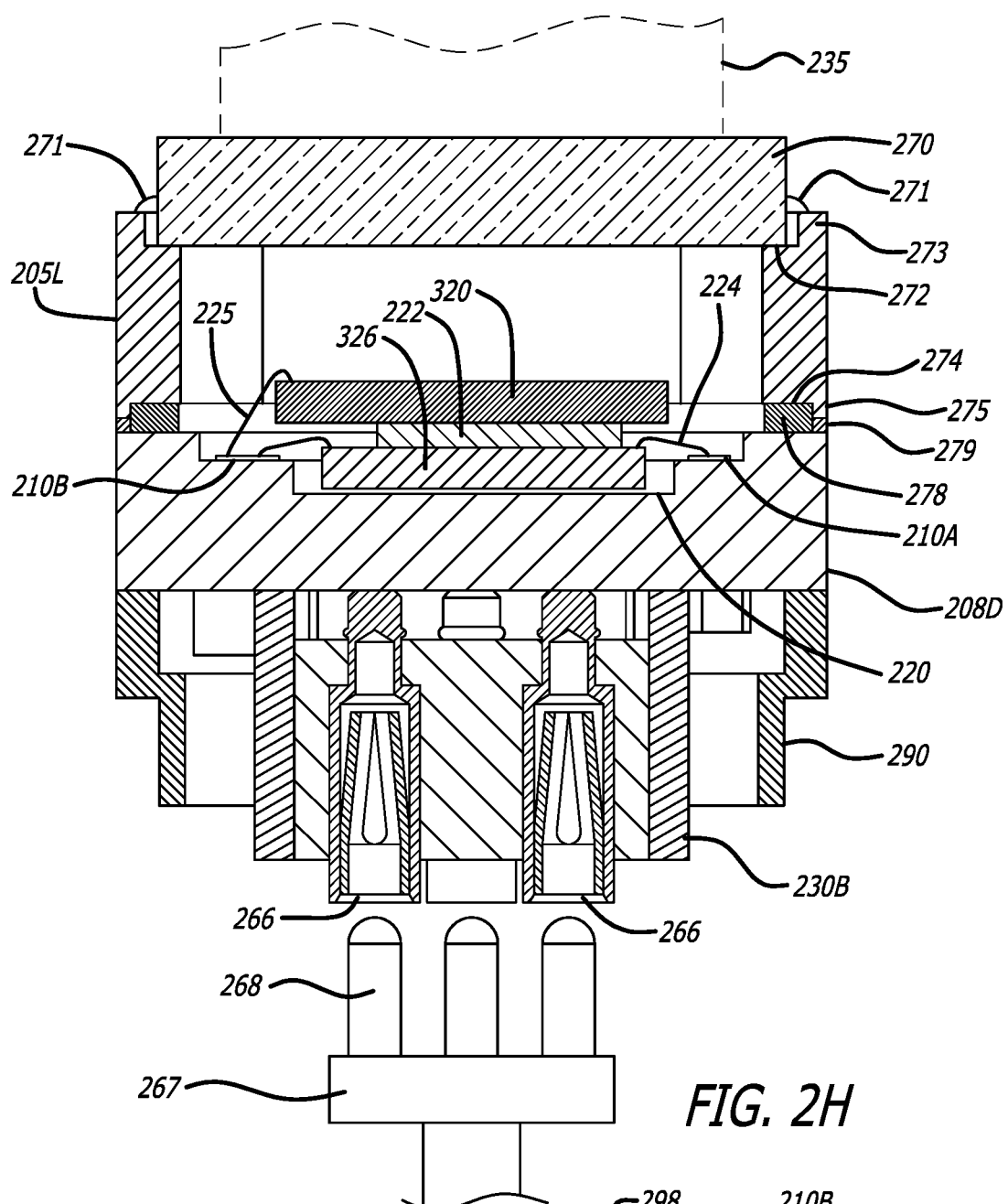
FIG. 2H is a perspective view of a subassembly of the inner housing of the cylindrical shaped camera module with upper and lower polygonal inner portions and cap assembly removed.

Referring now to FIG. 2H, a cross section view of a subassembly of the inner housing of the cylindrical shaped camera module is shown with upper polygonal inner portion, lower polygonal inner portion, and cap assembly removed. The inner housing 204B further includes a glass window 270 having lower edges of a bottom surface resting on a ledge 272 in the lower housing portion 205L. The glass window 270 is sealed on the ledge 272 using a glass frit sealant to form a glass frit seal 271, covering over an opening in the lower housing portion and forming a lower chamber for the opto-electronics. The window 270 is transparent to wavelengths of electromagnetic radiation captured by the image sensor. With the lower housing portion 205L supporting the glass window 207, the lower housing portion 205L may also be referred to as a frame. As discussed herein, a dry nitrogen gas may be introduced into the lower chamber as well as an upper chamber sealing off the lens barrels and the optics. The glass window 270 protects the image sensor 320 and the signal conditioning chip 326. The glass window 270 can further provide a mounting point for the ends of the lens barrels 235.

The ends of the optical or lens barrels 235 may rest and be attached by glue, UV cured epoxy, or cement to the top surface of the glass window 270 in a slight off axis alignment with axes of pixel arrays of the image sensor 320. The upper housing portion 205U (not shown in FIG. 2H) is welded to a shoulder portion 273 of the lower housing portion 205L.

A recess 274 in the bottom of the lower housing portion 205L forms a shoulder 275. The recess 274 receives a polygonal-shaped seal ring 278 in and near sides of the ceramic substrate 208D. The polygonal-shaped seal ring 278 may be formed of KOVAR and brazed onto the ceramic substrate 208D, in advance, to match thermal expansion of materials from heat. The lower housing portion 205L is also formed of KOVAR to match the thermal expansion coefficient of the ceramic substrate so that a hermetic seal survives sterilization during an autoclave process. A solder 279 is soldered into a gap between the shoulder 275 and the ceramic substrate 208D to hermetically seal the lower housing portion 205L to the ceramic substrate 208D. Portions of the ceramic substrate 208D may be metalized so the lower housing portion 205L formed of KOVAR may be attached with a metal to metal seal such as through brazing, soldering, or welding techniques.

The signal conditioning chip 326 is mounted in the cavity 220 with bond wires 224 on left and right sides coupled between bonding pads on the chip and bonding pads 210A-210B. An insulated spacer chip 222 is mounted on top of the signal conditioning chip 326. The stereo image sensor chip 320 is mounted on top of the spacer chip 222. Bond wires 225 on one side are coupled between bonding pads on the chip and bonding pads 210B of the ceramic substrate 208D. The ceramic substrate 208D acting as a hermetic barrier, also thermally matches the silicon of the signal conditioning chip 326 and the stereo image sensor chip 320.

An open hollow base cap 290 is coupled to the lower periphery of the ceramic substrate 208D to receive a potting material (e.g., silicon epoxy) to protect electronic and optoelectronic components that may be mounted to the bottom surface of the substrate.

Figure 2I:
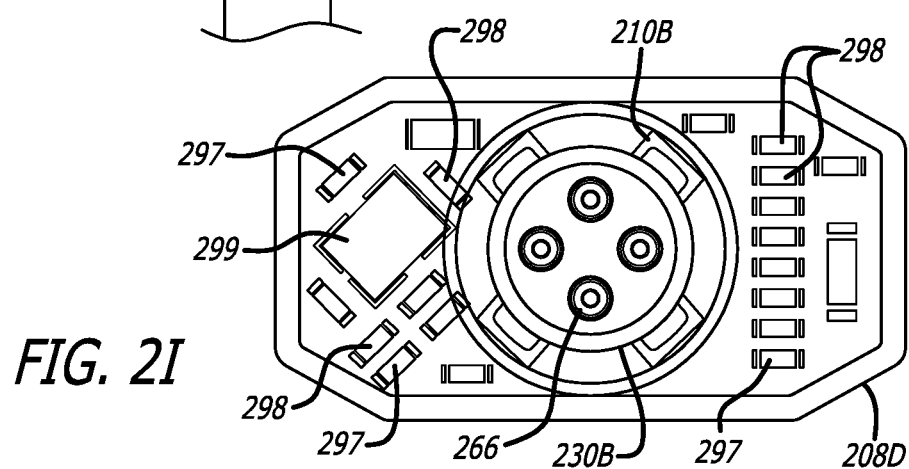
FIG. 2I is a bottom view of a subassembly of the inner housing of the cylindrical shaped camera module.

Referring now to FIG. 2I, a bottom view of the inner housing of the cylindrical shaped camera module is shown. A cylindrical surface mount connector 230B is mounted to outer pads 210B in the center of the outer surface of the ceramic substrate 208D. The size and central location of the connector 230B allow a plurality of chip resistors 297, a plurality of chip capacitors 298, and a crystal 299 to be mounted to outer pads 210B on the outer surface of the ceramic substrate 208D. The crystal 299 within an oscillating circuit generates an oscillating signal (e.g., a sine wave) that is used to generate a clock signal for the signal conditioning chip and the image sensor (see FIGS. 5A-5B, 6A-6B for example). The connector 230B includes pins 266 of a proper gender (e.g., female pins) that mate with pins 268 of the plug 267 with the opposite gender (e.g., male pins). The connector 230B allows four inner signal connections and one ground/shield outer cylindrical connection so that a quad-axial twisted pair cable can respectively provide power, serial communication signal, plus and minus differential video signals, and ground.

Figure 2J:
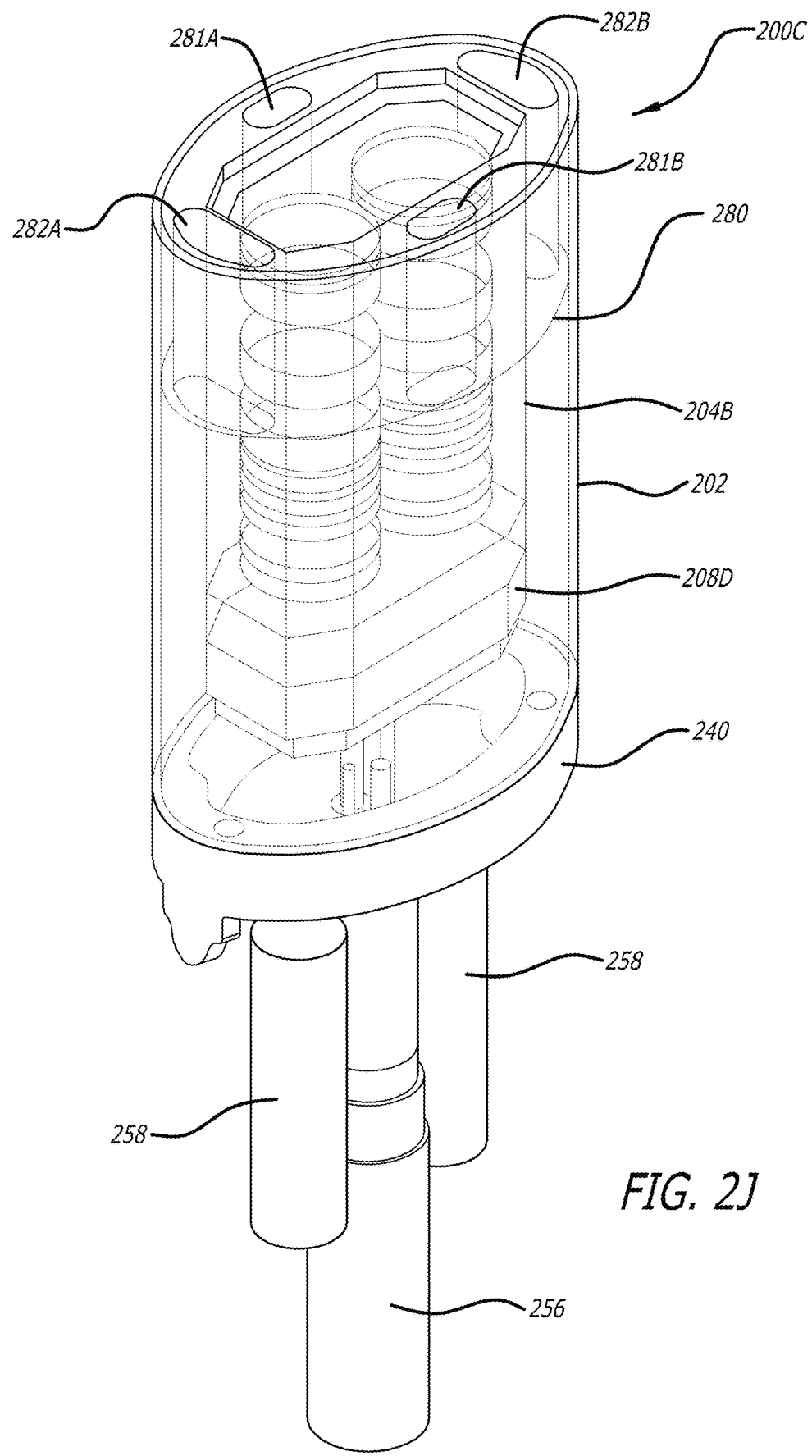
FIG. 2J is a side perspective view of an assembled cylindrical shaped camera module.

Referring now to FIGS. 2J, 2K, and 2L, assembled views of the minimally invasive surgical camera module 200C are shown. The minimally invasive surgical camera module 200C includes the outer housing 202 and the inner housing 204B with the ceramic substrate 208D, the window 270 and the surface mount connector 230B. To couple the assembled camera module 200C to the shaft 106 of the endoscopic camera instrument 101, the outer housing 202 is coupled to the distal end segment 240 of the joint 104 (see FIG. 1A).

The minimally invasive surgical camera module 200C further includes a cylindrical insert 280 near the distal instead between the walls of the outer housing 202 and the inner housing 204B. The cylindrical insert 280 extends down a portion of the height of the camera module. The cylindrical insert has a center opening to receive the upper hollow cylindrical housing portion and a plurality of radial spaced openings 281A-281B,282A-282B (see FIG. 2L) to receive groups or bundles of optical fibers 312 to form concentrated light areas. Optical fibers 312 routed through the instrument shaft are guided into the camera module by fiber sheaths 258. The optical fibers 312 are grouped together into groups and routed between the walls of the housings 202,204B and into the plurality of openings 281A-281B,282A-282B of the cylindrical insert 280.

The cylindrical insert 280 is formed out of an insulator or dielectric material (e.g., a high performance plastic such as ULTEM) to help electrically isolate the inner housing from the outer housing. Further, the cylindrical insert maintains alignment of the distal ends of the inner housing and the outer housing. Epoxy is inserted to backfill from the end of the cylindrical insert any remaining air space between the inner housing 204B and the outer housing 202.

FIG. 2L is a top view of the assembled cylindrical shaped camera module 200C. FIG. 2L shows an exemplary distribution of the optical fibers 312 into the openings 281A-281B,282A-282B of the cylindrical insert 280. As openings 281A-281B are closer to the center axis 229 of the camera module than the openings 282A-282B, a greater number of optical fibers are grouped into the side openings 282A-282B that the number of optical fibers grouped into the top and bottom openings 281A-281B to provide a more even overall light distribution about the distal end of the camera module.

Excess length of the optical fibers 312 extending beyond the front edge of the outer housing 202 may be removed by grinding and polishing. The distal ends of optical fibers 312 are ground and polished flush with the edge of the outer housing 202, leaving a smooth polished edge between the outer housing 202 and the sapphire window 206A,206B. A polished edge of the optical fibers 312 can emit more light and can be easier to clean, disinfect, and sterilize.

Figure 3A:
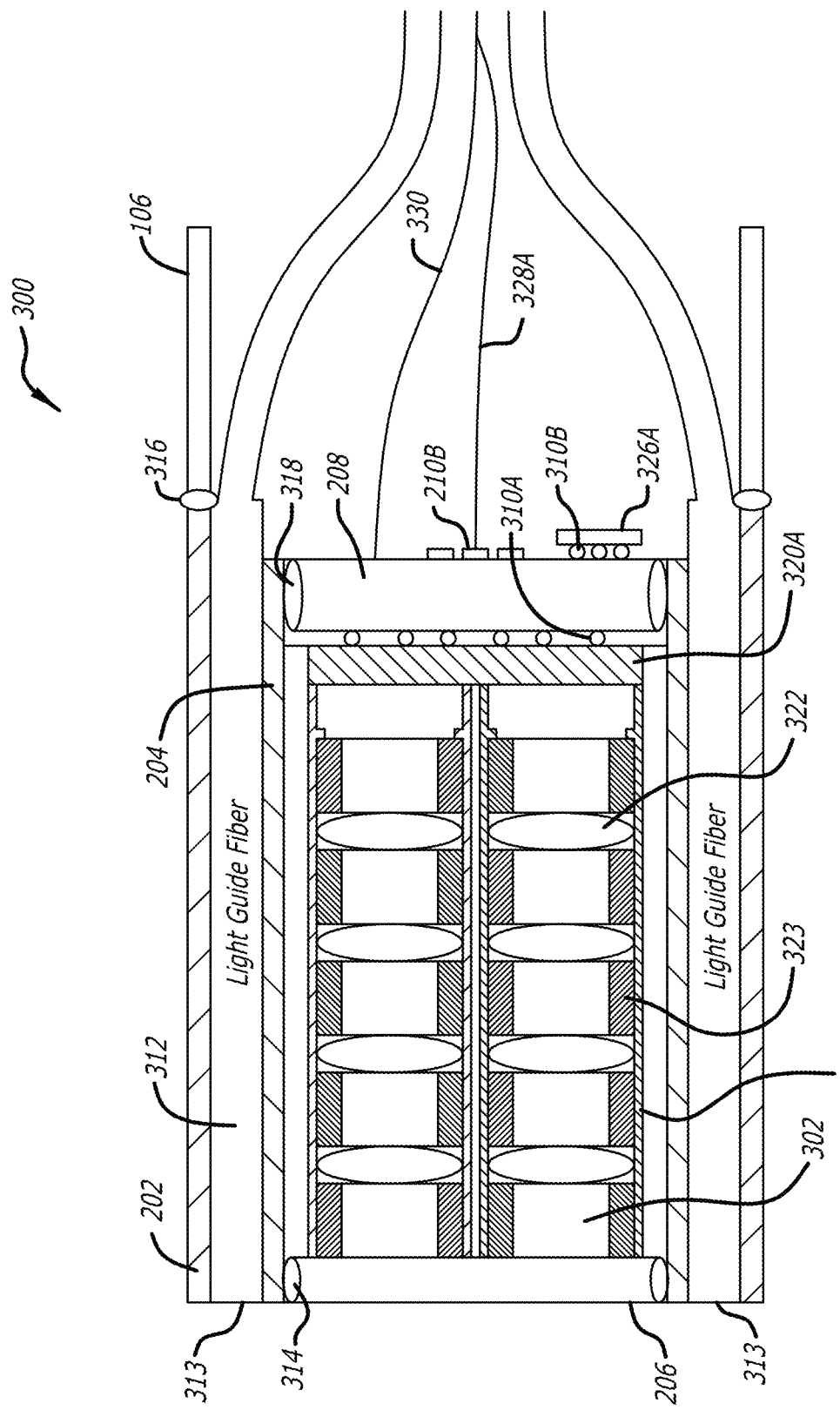
FIG. 3A is a side diagrammatic view of a coaxial double walled cylindrical shaped camera module.

FIG. 3A is a diagrammatic view of a camera module 300 coupled to the instrument shaft 106 at a weld point 316. The camera module 300 is an instance of the camera module 100 previously described in the endoscopic camera system 100 of FIG. 1A.

The camera module 300 generally employs the housing structure 200A,200B,200C described previously with reference to FIGS. 2A-2L A hollow stainless steel, titanium, aluminum, or metallic alloy (e.g., KOVAR) cylinder may form the outer housing 202 of the camera module 300. A hollow metal or metallic alloy (e.g., KOVAR, a nickel-cobalt ferrous alloy) cylinder may form the inner housing 204A,204B. To couple the assembled camera module 300 to the shaft 106 of the endoscopic camera instrument 101, the outer housing 202 may be laser welded to the distal end (segment 240) of the joint 104 (joggle joint and wristed joint as mentioned herein).

Nestled between the walls of the outer housing 202 and the inner housing 204A,204B are the optical fibers (may also referred to as light guide fibers) 312. The optical fibers 312 may be evenly distributed to surround the inner housing 204A. To evenly distribute the light in a halo shape around the inner housing 204A, multiple individually fine strands of optical fiber may be bound together with epoxy and preformed into a tubular shell for insertion between the outer housing 202 and the inner housing 204A. Alternatively, the optical fibers 312 may be lumped together in areas about the inner housing 204B with a dielectric epoxy 250B filling the gaps between the inner housing 204B and the outer housing 202 as shown in FIG. 2B. Excess length of the optical fibers 312 extending beyond the front edge of the outer housing 202 may be removed by a grinding and polishing process. The distal ends of optical fibers 312 are ground and polished flush with the edge of the outer housing 202, leaving a smooth polished edge 313 between the outer housing 202 and the sapphire window 206A,206B. A polished edge 313 of the optical fibers 312 may emit more light and may be easier to clean, disinfect, and sterilize.

The distribution of the optical fibers 312 surrounding the inner housing 204A,204B and a dielectric epoxy 250B may also serve to electrically isolate the inner housing (and the components therein). The inner housing 204A,204B of the camera module may be grounded to reduce noise. One or more of the cylindrical insert 280, the optical fiber 312, and the dielectric epoxy 250B can provide a high voltage dielectric barrier to help isolate the grounded portions of inner housing 204A,204B from the outer housing 202 and isolate a patient from ground to help meet cardiac float (CF) and/or body float (BF) safety and electro-magnetic compliance for medical systems in physical contact with a patient (e.g., see IEC specification IEC60601). Portions of the inner housing 204A,204B may be further isolated from making patient contact so that materials that may be less biocompatible can be used in the design of the inner housing.

Figure 3B:
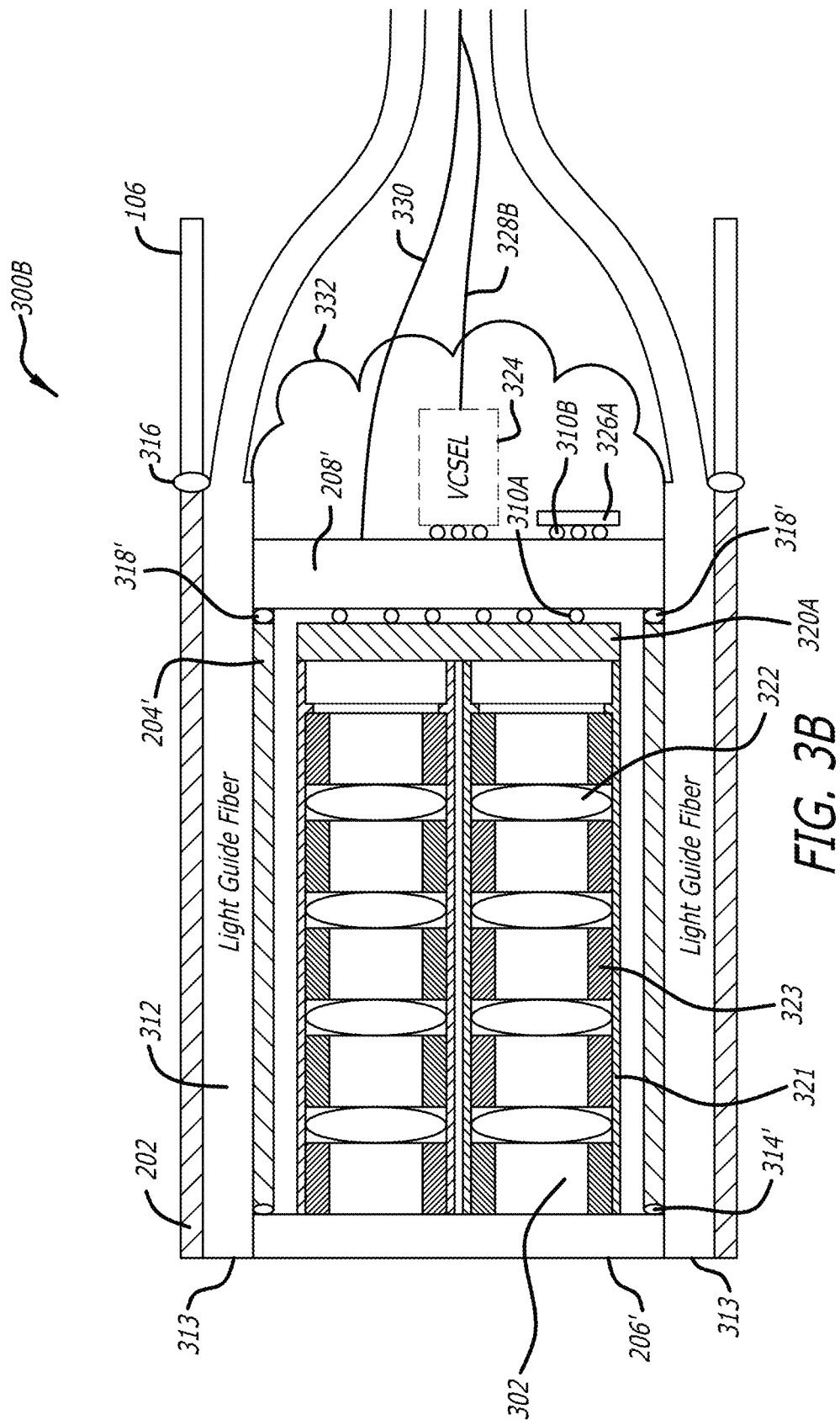
FIG. 3B is a side diagrammatic view of another coaxial double walled cylindrical shaped camera module.

In one embodiment, the sapphire window 206A,206B may be coupled to the inner side of inner housing 204A, 204B flush with the distal edge of inner housing and the polished edge of optical fibers 312. To hermetically seal the sapphire window 206A,206B to inner housing 204A,204B forming the hermetic seal 314A, 314B, a gold solder may be used as the sealant. To solder sapphire window 206A,206B onto a metallic surface, the edge of sapphire window to couple to the housing may be metalized to aid adhesion of the gold solder. At the proximal end of inner housing 204A,204B, the ceramic substrate 208, 208',208A,208B is attached to the inner housing by a laser welding process. The cross section of weld joint forming the hermetic seal 318, 318' is shown in FIGS. 3A-3B as being a hollow oval shape. However, the weld joint may be flat and in the shape of a band around the periphery of the ceramic substrate 208,208'. With both ends of inner housing 204A,204B hermetically sealed, the optics and electro-optics of the camera module 300 may be protected during an autoclave cycle of the instrument 101.

Behind sapphire window 206A,206B is a pair of lens barrels 302 that are an example of the lens barrels 235 shown in FIGS. 2F and 2G. Each lens barrel 302 may include a hollow tube 321, a plurality of lenses 322, and a plurality of hollow spacers 323 interspersed between a lower inner stop ring and a top edge of the hollow tube. Each lens barrel 302 may hold the plurality of lenses 322 along optical axes substantially perpendicular with the image sensor 320. Light passing through sapphire window 206A,206B is focused by lenses 322 onto active pixel areas of the image sensor 320A,320B. The image sensor 320A,320B is a stereo analog or digital image sensor with active pixel areas that may be a CCD, a CMOS camera sensor, an intensified charge-coupled device (ICCD), etc. to capture stereo color or stereo monochrome images of the surgical site. With an analog image sensor, an analog to digital converter may be used to convert the analog image signals into digital image signals to provide noise immunity. The sensor 320A,320B may capture visible electromagnetic (EM) radiation within the visible EM spectrum as well as other ranges of EM radiation outside the visible EM spectrum.

Instruments, such as an endoscopic camera, used in endoscopy are small to fit into entry port incisions or natural entry points of a patient. To accelerate post surgery recovery, endoscopy reduces tissue damage. Thus, in general, the smaller the tool, the better. Thus, it is desirable to reduce the size of the image sensor to provide a smaller endoscopic camera module. To provide better image resolution, however, it is desirable to provide more active pixels in the image sensor.

In one embodiment, the number of active pixels on the front of the image sensor may be maximized by separating the capturing function of the photoactive region of the image sensor from the processing function. (e.g., see FIGS. 6A-6B) By separating the two functions, a greater amount of die area may be used for a photoactive region of the image sensor relative to the die's overall area. This relatively larger photoactive region allows for a larger number of pixels to be formed, which enables higher definition stereo images to be captured. Alternatively, the die area of the image sensor may be reduced to provide a smaller cross section of the endoscope without sacrificing image resolution provided by an image sensor having a relatively larger die area. As discussed further herein, the image capturing function may be separated from the signal processing function into two chips to meet space requirements. The integrated circuit chips may be shielded and/or spaced apart from one another to provide better signal quality as well (e.g., see FIGS. 5A, 5B, 6A, and 6B, and their associated text.)

Image sensor 320A having ball grid array contacts is mounted onto inner pads 210 of the ceramic substrate 208A. The solder balls 310A are coupled to the inner bond pads 210 on the inner surface of ceramic substrate 208A and a surface of the image sensor 320A. The solder balls 310B of the signal condition processor 326A are coupled to second bond pads 210 on the outer surface of ceramic substrate 208A and a surface of the processor 326A. Traces within the substrate 208A connect inner bond pads 210 to outer bond pads 210 so that the image sensor 320A can couple to circuitry and electrical cables outside the hermetic seal 318. Conductive layers, metallic traces, redistribution layers (vias), and/or wire leads may be embedded or printed on the inner layers of ceramic substrate 208A to connect the first set of bond pads on the inner surface to the second set of bond pads on the outer surface of ceramic substrate 208A (e.g., see FIGS. 5A-5B and description thereof).

Using a multilayer co-fired ceramic substrate allows connection through the substrate without the use of via tubes. Via tubes are glass or plastic tubes embedded in the ceramic substrate, through which wires may be threaded to connect circuitry on opposite sides of a substrate. The use of via tubes is labor intensive, because each tube connection is normally made by hand. Furthermore, via tubes may have gaps between wire and tube that may require sealant or potting material. Thus, the use of a multilayer ceramic substrate may be preferable for a camera module that will undergo autoclaving.

Connection between the hermetically sealed image sensor 320A and the processor 326A may be made by the traces within the substrate 208A. Bond pads 210B of the substrate 208A may also be use to electrically connect to the signal cable 328A to transmit video data out to CCU 112.

Processor 326A mounted to the outer surface of ceramic substrate 208A processes analog image data Ain from image sensor 320A and generates digital image data output Dout. Power, digital ground, and analog ground signals for the image sensor 320A, processor 326A, and other components in the camera module 300 may be provided for by electrical conductors in cable 330. The cable 330 may also have one or more control signal conductors or wires to control the camera module to start and stop video capture, for example.

In FIG. 3B, a schematic diagram of a cylindrical camera module 300B is shown. The similarly numbered components shown in FIG. 3B in comparison with FIG. 3A were previously described and are incorporated herein by reference so that they are not being described again for the sake of brevity.

In the cylindrical camera module 300B, the distal edge of inner housing 204' is slightly shorter than distal edge of the outer housing 202. This gap allows the sapphire window 206' to be soldered to the leading edge of inner housing 204' so that the outer surface of the window is flush with the edge of the outer housing 202 as shown. In the previously described embodiment in shown in FIG. 3A, the sapphire window 206A,206B was soldered to the inner edge of inner housing 204A. Gold solder is used to solder the sapphire window 206' flush with the outer housing 202 and to form the hermetic seal 314' between the inner surface of the window 206' and the edge of the inner housing 204'. In either case, the front of camera module 300B presents a smooth surface to reduce the number of crevices and aid cleaning.

In another embodiment, a vertical cavity surface emitting laser (VCSEL) 324 may be used for optical fiber data transmission as shown in FIG. 3B. VCSELs are capable of delivering over one gigabit per second (Gbit/s) of data transmission over optical fibers at temperatures of up to 60° C. As mentioned before, a surgeon's ability to perform precise, meticulous endoscopic surgery is enhanced by the surgeon's ability to view the surgical field in detail. High definition cameras may be used to deliver sharp contrasted images that a surgeon can see during surgery. The VCSEL 324 may be able to transmit the high definition images over the optical fiber 328B to the camera control unit and/or the surgeon's monitor. Another advantage of using fiber optic data transmission is the elimination of cross talk or signal interference from other electronic signals (e.g., control signals) and its immunity to electrocautery interference.

Processor 326A and VCSEL 324 may be encapsulated by a sealant or temperature/moisture resistant potting material 332. The processor 326A and VCSEL 324 are candidates for encapsulation because they do not need to directly receive light images focused by lens 322. By separating the functions of image sensor 320A, processor 326A and VCSEL 324 into different chips, the image sensor 320A may be hermetically sealed with other optical components behind sapphire window 206. Light may pass though sapphire window 206 to impact upon the image sensor 320A, while the processor 326A and VCSEL 324 may be placed behind the ceramic substrate 208A and encapsulated by sealant or potting material 332. Placement of processor 326A and VCSEL 324 outside the inner may aid replacement of either component in case of failure.

Another embodiment may use utilize a combination fiber optic/copper co-axial cable connected to a short length of ribbon cable to transmit data to CCU 112. Briefly referring back to FIG. 2B, a co-axial cable 256 is connected to a ribbon cable 238 and threaded through the end segment 240 of the joint 140. The plurality of cables 242 may be shielded from "noise" and cross-talk by individually sheathing each cable in a non-conductive covering. Similarly sheathing 244 and 246 may further isolate the cables from outside noise as well as physical damage. The segment 240 of the joint 140 may be connected to the proximal end of camera module 102. Specifically, the segment 240 may be welded to camera module 102 at the weld point 316 shown in FIGS. 3A-3B. The joint 140 may be a wristed joint or a portion of a joggle joint that is described in U.S. patent application Ser. No. 11/762,165, entitled MINIMALLY INVASIVE SURGICAL SYSTEM, filed by Larkin et al. on Jun. 13, 2007. The use of a pluggable cable 238 may be advantageous in the assembly process. As mentioned previously, connector 230 may be surface mounted to the back side of substrate 208 for quick disconnect of cable 238 and replacement of camera module 102.

Isolation and Grounding

Figure 5A:
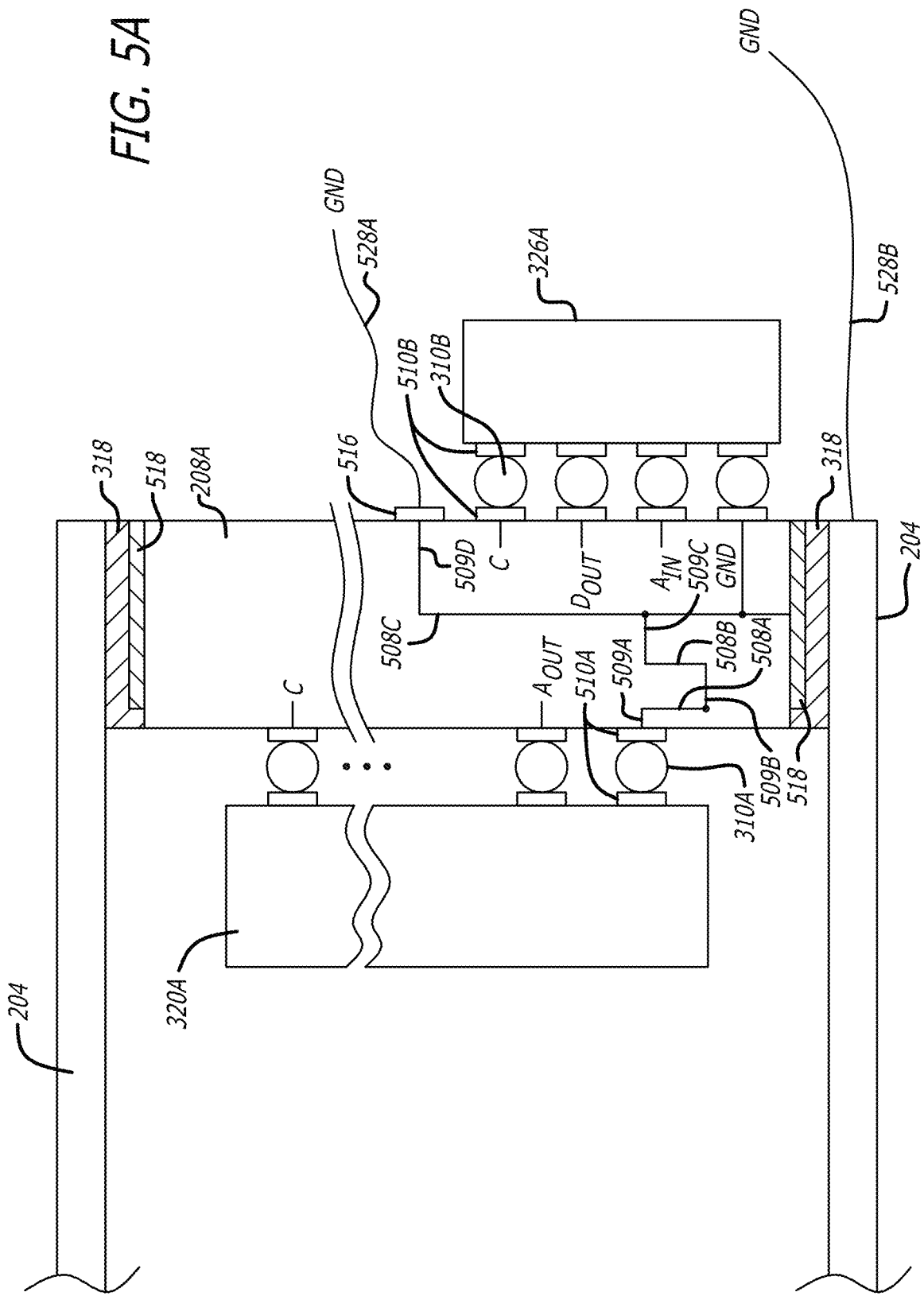
FIG. 5A is a magnified side schematic view of the camera module illustrated in FIGS. 3A-3B.
Figure 6A:
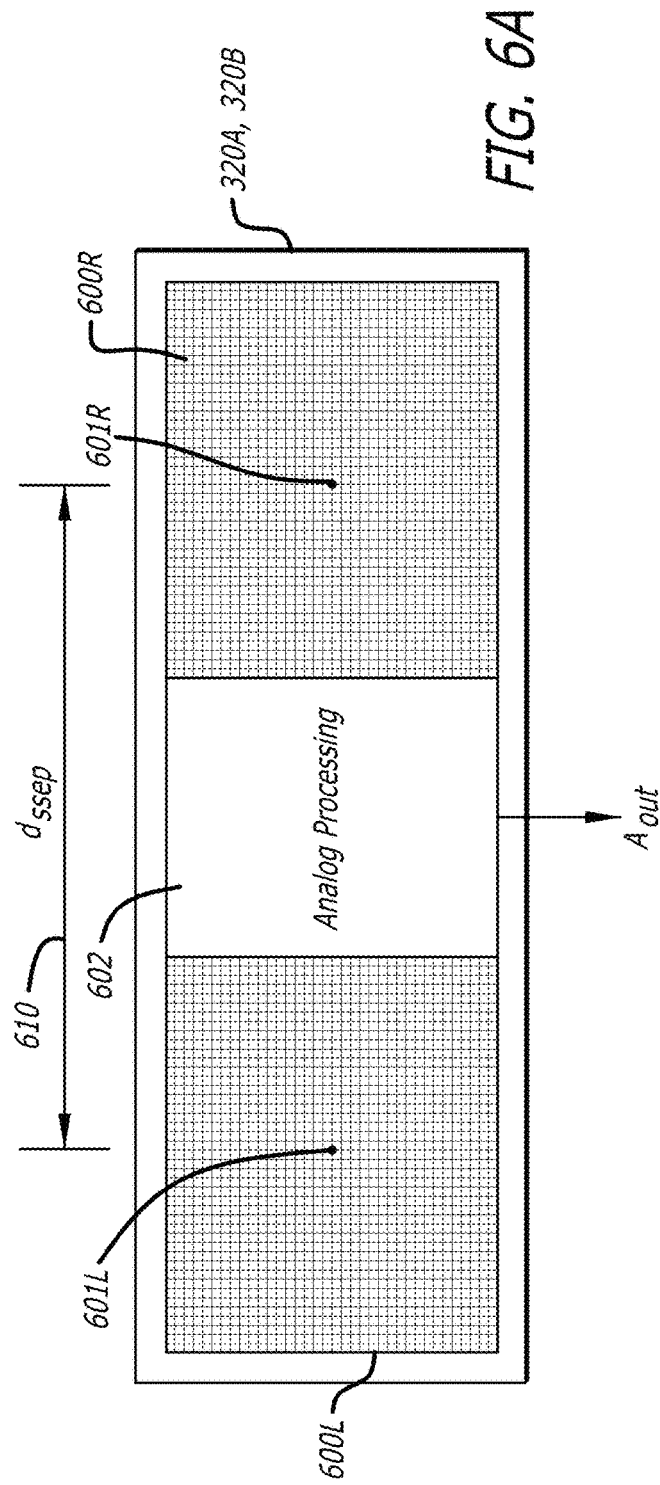
FIG. 6A is a block diagram of a stereoscopic image sensor.
Figure 6B:
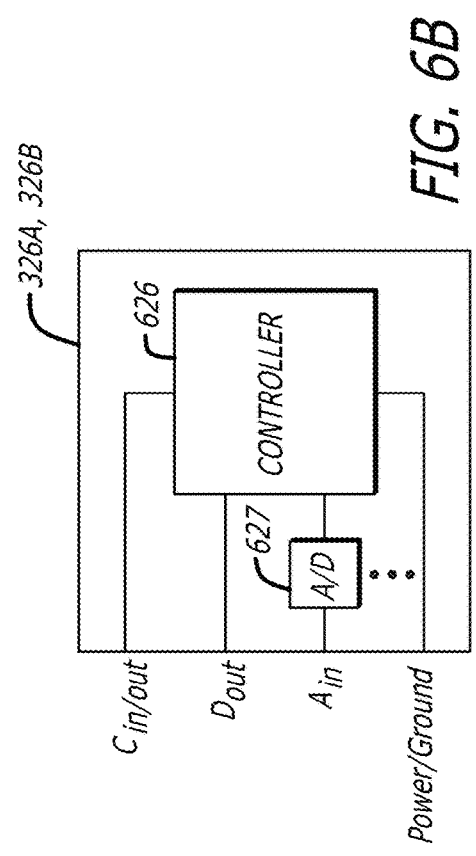
FIG. 6B is a block diagram of a controller/processor/converter for the stereoscopic image sensor of FIG. 6B.

Referring now to FIGS. 5A and 6A-6B, aspects of the camera module are illustrated in further detail. In response to control signals C, the image sensor 320A has at least one pixel array (e.g., see left and right pixel arrays 600L,600R shown in FIG. 6A) that captures analog signals Aout. The signal conditioning processor 326A,326B includes an analog to digital (A/D) converter 627 and a controller 626. A substantial portion of the digital signal processing and the analog to digital conversion is performed by the processor 326A,326B. With signal conditioning functions moved to the processor 326A,326B, one or more pixel arrays may be made larger to support capturing stereo high definition images on a single chip. With the processor 326A,326B and the image sensor 320A,320B provided on separate chips, they may make separate connections to power and ground terminals of a power supply with separate wire bonds for example.

Although isolating the image sensor 320A from the processor 326A by placing them on opposite sides of ceramic substrate 208A may have some advantages, it is also feasible to stack the chips one above the other. The image sensor 320A may be stacked above the processor 326A, in parallel or perpendicular to each other, and both chips may be placed within the cutout recess 220. In such an arrangement, the chips 320A,326A are protected within the hermetic seal of the inner housing 204 and may be wire bonded to the ceramic substrate. Alternatively, through-hole silicon via technology may be used to have the chips 320A-326A connect to each other and the ceramic substrate.

The ceramic substrate 208A may include pads 510A on one side to couple to the image sensor 320A and pads 510B on an opposite side to couple the processor 326A. The image sensor 320A includes corresponding pads 510A coupled to the solder balls 310A that are coupled to the pads 510A of the substrate 208A. The processor 326A includes corresponding pads 510B coupled to the solder balls 310B that are coupled to the pads 510B of the substrate 208A. The analog to digital converter 627 is coupled to one or more pads 510B to receive analog input signals Ain. The signal processor 626 is coupled to one or more pads 510B to drive control signals C and digital data signals Dout as well as receive control signals. The digital data signals D represent portions of one or more captured stereo images captured by the image sensor. The digital data signals D are sent from the camera module and the instrument 101 to the camera control unit CCU 112 (see FIG. 1A) for further processing (e.g., decoding/translating, error detection/correction, image shifting) of stereo image data before being displayed by the stereo viewer 118A,118B. The digital data signals D are sent as differential digital data signals over a pair of conductors to provide a more robust noise immune signal into the camera control unit 112.

For power, ground, and signals (A,C) to route from one side of the ceramic substrate 208A to the other, the ceramic substrate includes a plurality of metal layers 508A-508C with metal traces coupled between pads 510A-510B to seal moisture out. Exemplary substrates with layers of metal traces are described in further detail in U.S. Pat. No. 5,635,301 (Kondo et al.); U.S. Pat. No. 6,228,468 (Vodrahalli); and U.S. Pat. No. 6,891,266 (Kinayman et al.), all of which are incorporated herein by reference. The moisture proof seal provided by the ceramic substrate 208A is important to keep moisture from the image sensor 320 and the lenses 322 in the lens arrays 302 of the camera.

The endoscopic camera may be part of an entry guide that comes in contact with a patient. In which case, it is desirable to allow the outer housing 202 of the camera module and the shaft of the endoscopic camera to electrically float so that it does not inadvertently provide an electrical path to ground. However to improve signal to noise ratios for the signals transmitted from the camera module, the inner housing 204A,204B of the camera module may be grounded if barriers are used to avoid the inner housing from making contact with the patient. Additionally, signals may be transmitted as a differential signal with an error correction code (ECC) and/or shielded within a shielded cable to improve signal to noise ratios.

The inner housing 204A,204B is formed of an electrically conductive material to ground it out to reduce electrical noise and improve signal transmission from the camera module. With the inner housing 204A,204B grounded, electrical noise around the image sensor 320A,320B may be further reduced so that less noise may be coupled into signals. With the inner housing 204A,204B grounded, the inner housing is electrically isolated from the outer housing 202 that is to electrically float.

The optical fiber 312 arrayed around the inner housing 204A,204B between the inner and outer housings may electrically isolate a grounded inner housing from a floating outer housing 202. A non-conductive adhesive (e.g., dielectric epoxy 250B shown in FIG. 2B) may be applied to the array of optical fiber 312 to fill in gaps between strands of optical fibers and the inner and outer housings for further electrical isolation.

As shown in FIG. 3B, an end of the inner housing 204' does not extend as far out as the end of the outer housing 202. The window 206' is coupled on top of the end of the inner housing 204 with a hermetic seal 314' as shown to prevent moisture from entering the inner cylindrical subassembly. The window 206' being formed of a non-conductive material, such as sapphire, is an insulator and electrically isolates the grounded inner housing 204 from tissue in a body cavity during surgery. A non-conductive potting material 332 may also cover over the opposite end of the inner housing 204', the substrate 208A, the processor 326A and the VCSEL 324 to further electrically isolate the grounded inner housing 204 from the floating outer housing 202. The potting material 332 also keeps moisture from the processor 326A, the VCSEL 324 and any other electrical component at the end. In this manner, the cylindrical inner housing 204' is substantially electrically isolated from the outer housing 202 and any tissue that the camera module may come in contact with. Alternatively, the cylindrical inner housing 204' may also be allowed to electrically float and the signals may be transmitted as a differential signal with an error correction code (ECC) and/or shielded within a shielded cable.

Area Conservation

Referring now to FIG. 5B, alternate aspects of the camera module are illustrated. In this case, the image sensor 320B mounts to the processor 326B in a stacked configuration within the inner can 204A,204B to provide a large image sensor while conserving the cross sectional area of the endoscope. The pad 510C on each are coupled together by the solder balls 310C. The processor 326B in turn mounts to the substrate 208B to electrically couple to the pins 526 through the solder balls 310A and the pads 510A. Alternatively, the pads 510A of the processor 326B may be wired bonded to the pads 510A of the substrate 208B.

Power, ground, and control signals from the pins 526 may be coupled into the processor 326 through the substrate 208B by way of the pads 510A and the solder balls 310A. Power, ground, and control signals may couple from the pins 526 to the image sensor 320B through the processor 326B. One or more vias 529 may couple a pad 510A on one side of the processor 326B to a pad 510C on the opposite side to route power, ground, and/or control signals from one side of the chip to the other. Alternatively, a trace may route around the edge of the chip from one side to the other. Analog signals Aout from the image sensor 320B may couple into the analog input Ain of processor 326B through the pads 510C and solder balls 310C.

Male pins 526 may couple to female pins 566 in a connector 560 which are coupled to the cable routed through the shaft of the endoscope for the camera module to receive power, ground, and control signals and transmit data to the camera control unit.

One or both of the image sensor 320B and the processor 326B may include a ground plane 521A,521B to shield the analog circuits of the sensor 320B from digital noise that may be generated by the processor 326B.

Stereo Image Convergence

Figure 7:
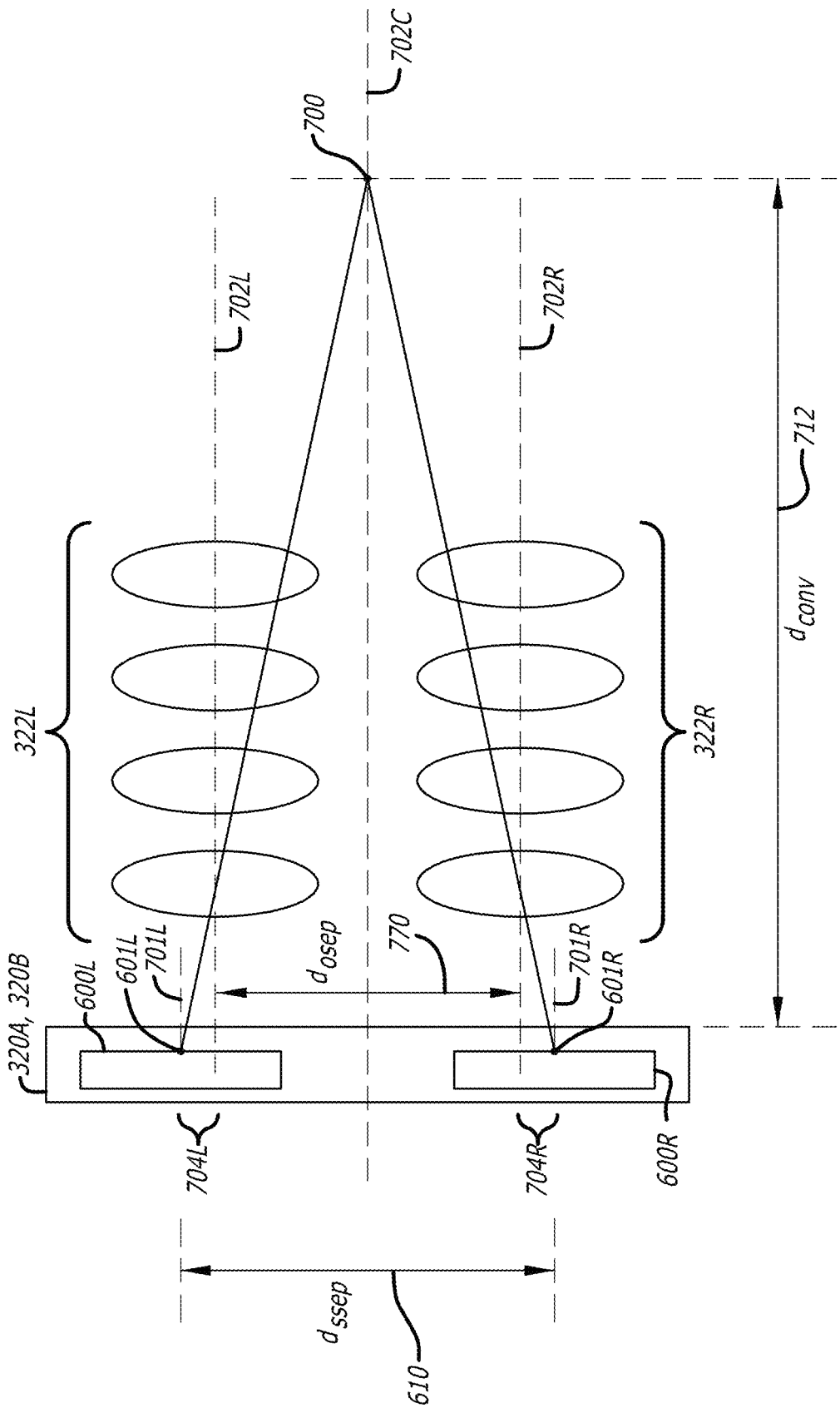
FIG. 7 is a diagrammatic diagram illustrating the left and right pixel array offset from the optical axis for stereo image convergence.

Referring now to FIGS. 6A and 7, a stereoscopic endoscope requires image convergence to provide proper stereo images and depth perception to a pair of human eyes with pupil separation. One way of providing image convergence is to slightly angle each of the left and right lenses into left and right image sensors. Another method of providing image convergence is to offset the center of left and right image sensors from respective left and right optical axes of the left and right lens arrays without any change in optical axes. The centers of left and right captured images may also be similarly offset to the centers of left and right displays by image shifting for image convergence when displayed by a stereo viewer to improve stereo imaging effects.

FIG. 6A illustrates a stereoscopic image sensor 320A, 320B with a left pixel array 600L and a right pixel array 600R separated by analog processing circuitry 602. The left pixel array 600L, the right pixel array 600R, and the analog processing circuitry 602 are on the same monolithic silicon die, avoiding having to align the left and right pixel arrays relative to each other. The left pixel array 600L has a left pixel center 601L and the right pixel array 600R has a right pixel center 601R. Each of the pixel arrays 601L,601R may be an array of 1280 pixels wide by 1080 pixels high, for example, to provide a relatively high definition stereo image. The left pixel center 601L and the right pixel center 601R are separated by a sensor separation distance Dssep 610.

The left pixel array 600L and the right pixel array 600R are horizontally read out along rows of pixels in each by the analog processing circuitry 602. The analog processing circuitry 602 to read each array is co-located between the arrays 600L and 600R to reduce circuit area and overall die size of the image sensor.

FIG. 7 illustrates how the center of the left and right image sensors are offset from the respective left and right optical axes of the left and right lens arrays for stereo image convergence. The center axis of each lens in the left lens array 322L is aligned to a left optical axis 702L. The center axis of each lens in the right lens array 322R is aligned to a right optical axis 702R. A left pixel center axis 701L extends through the left pixel center 601L substantially perpendicular to a layer of the left pixel array 601L. A right pixel center axis 701R extends through the right pixel center 601R substantially perpendicular to a layer of the right pixel array 601R. The left pixel center axis 701L, the right pixel center axis 701R, the left optical axis 702L and the right optical axis 702R are substantially parallel to each other. Each may also be substantially parallel to a center axis 702C. However for image convergence, the left pixel center axis 701L is not coaxial with the left optical axis 702L. Nor is the right optical axis 702R coaxial with the right pixel center axis 701R, It is desirable to have stereo image convergence at a point 700 along the center axis 702C that is a distance Dconv 712 away from a plane (e.g., a surface of the sensor 320A,320B) passing through the left pixel center 601L and the right pixel center 601R. To provide the stereo image convergence, the left pixel center 601L of the left pixel array 600L is shifted out from the left optical axis 702L of the left lens array 322L by a left pixel array offset 704R. The right pixel center 601R of the right pixel array 600R is shifted out from the right optical axis 702R of the right lens array 322R by a right pixel array offset 704R. In this manner, the sensor separation distance Dssep 610 is greater than an optical separation distance Dosep 710 between the left optical axis 702L and the right optical axis 702R.

Rectangular Endoscopic Camera Module

The housing of the camera module may have other shapes and may have a pluggable connector to plug into a receptacle in the shaft of endoscopic camera. For example, the housing of the camera module may be circular or rectangular. The pluggable camera module at the tip of endoscope may be a single use disposable camera tip module that is discarded after each surgery. In which case, the disposable pluggable camera module does not require sterilization by autoclaving after surgery. Instead of being designed to survive autoclaving, the disposable pluggable camera module is designed for low cost.

Figure 4A:
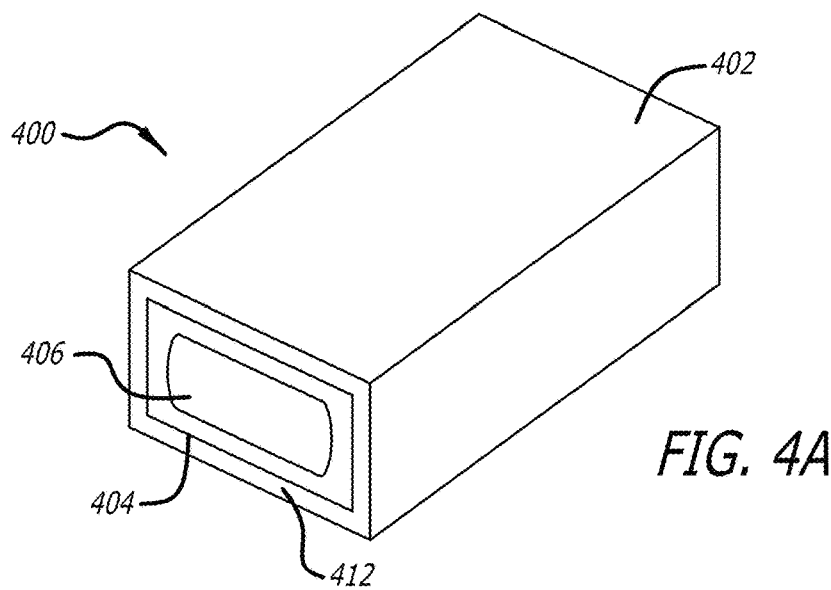
FIG. 4A is a perspective view of a rectangular shaped camera module.

Referring now to FIG. 4A, a rectangular camera module 400 is illustrated in another embodiment. The rectangular camera module 400 includes an outer rectangular housing 402, an inner rectangular housing 404, a window 406, and an array of optical fibers 412. The outer rectangular housing 402 and a portion of the inner rectangular housing 404 are preferably formed out of other moisture proof materials such as stainless steel or KOVAR.

Figure 4B:
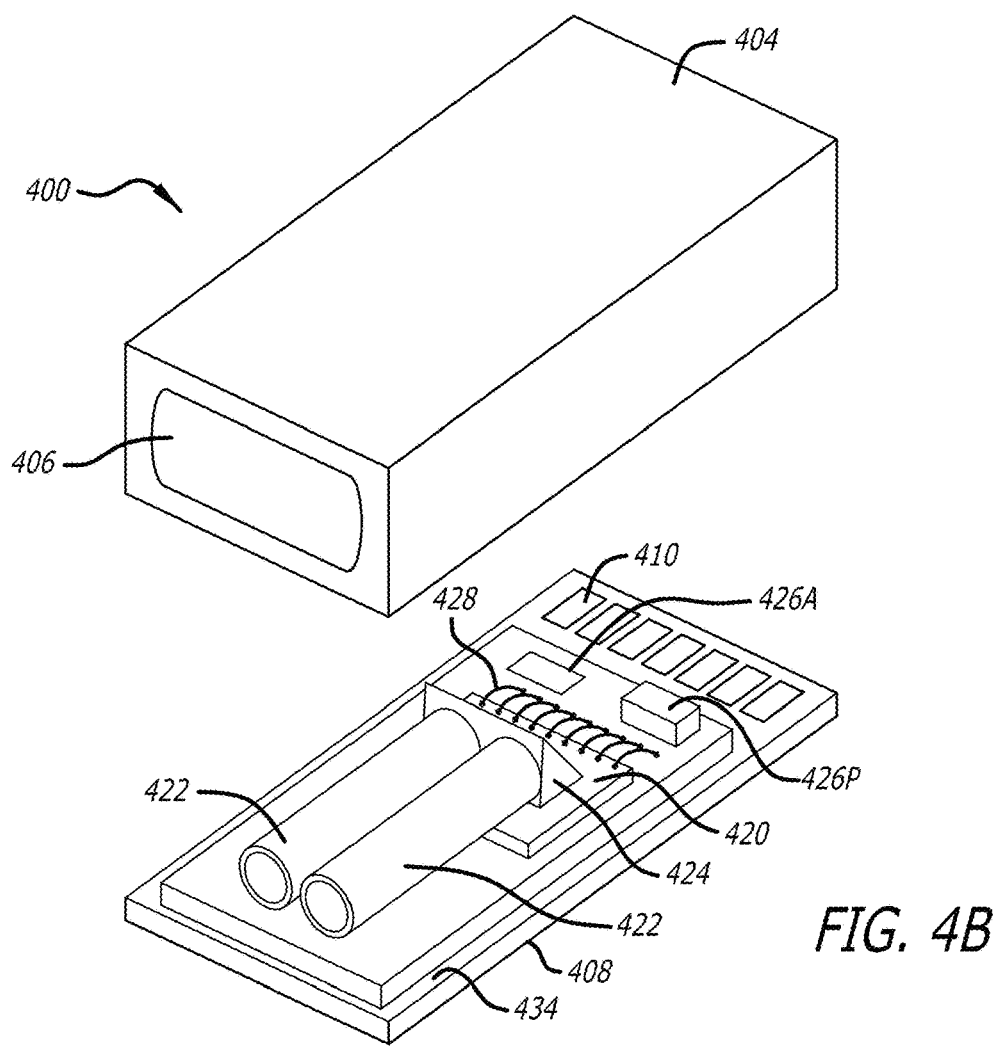
FIG. 4B is perspective view of a rectangular shaped camera module with both housings removed.

FIG. 4B illustrates an exploded view of an inner subassembly with the inner housing 404 decoupled from a ceramic substrate (base) 408. As shown in FIG. 4B, the inner rectangular stainless steel housing 404 is enclosed on five sides like a rectangular box but with an open bottom that is closed by the substrate 408. The substrate 408 may include a housing mounting pad 434 to receive the inner housing 404 and seal the optic, optical electrical, and electrical elements therein. The window 406 is set into an opening at the distal end of the inner rectangular stainless steel housing 404. The window 406 is hermetically sealed within an opening at a front end of the inner housing 404.

The window 406 may be made of any suitably scratch, heat, moisture, and solvent resistant material that is also transparent to a range of wavelengths detected by the image sensor 420 behind the window. In one embodiment the window is a sapphire window 406 brazed onto the inner housing 404. To braze a sapphire window 406 onto a metallic surface, the peripheral edge of sapphire window 206 may be metalized to aid adhesion. In other embodiments, the sapphire window 406 may be soldered onto inner housing 404 using a gold solder.

The inner rectangular stainless steel housing 404 is hermetically sealed to the ceramic substrate 408 through welding or other techniques to form a base and close the open side of the inner housing 404. Optical fibers 412 surround the first housing 404. The outer steel housing 402 is open at a front end and a back end. The outer housing 402 slides over the optical fibers 412 around the first housing 404.

In between the inner housing 404 and the outer housing 402 are arranged the plurality of optical fibers 412. The optical fibers 412 may occupy the entire space between inner housing 404 and outer housing 402 such that light launched out from optical fiber 412 may form a halo around the front of inner housing 404. An adhesive may be used to fill in gaps between the fibers 412 as well as between the inner housing and outer housing. Alternatively, an end portion of the optical fibers 412 may be molded together to fit within the gap between the inner housing and outer housing with an adhesive filling any gaps. In another embodiment, the optical fiber 412 may be bundled and routed to discrete point or points on the front of camera module 400, providing a more localized light source.

In FIG. 4B, a subassembly of the rectangular endoscope camera module 400 is exposed with the inner housing 404 lifted up and the fibers 412 and outer housing 402 not shown. The inner housing 404 is lifted off of ceramic substrate 408 to expose the electrical, optical, and electro-optical components inside the camera module. As previously mentioned, it may be beneficial to substantially match the thermal expansion of the inner housing 404 to that of the ceramic substrate 408. Forming the inner housing 204 out of a substance such as nickel-cobalt ferrous alloy may reduce stress on the ceramic substrate due to thermal expansion during an autoclave cycle.

Mounted over ceramic substrate 408 are a pair of objective lenses 422 (one each for left and right images of a stereo image), a mirrored prism 424, and an image sensor 420. The objective lenses 422 are secured such that light passing through the sapphire window 406 along their optical axes is focused into the mirrored prism 424. The mirrored prism 424 redirects the light at a right angle to its original path along the optical axes onto the image sensor 420 that is mounted to the substrate 408.

As with previously described embodiments, image sensor 420 may be a charged-couple device (CCD), a CMOS sensor, an intensified charge-coupled device (ICCD), etc. To maximize the number of active pixels on the front of the image sensor 420, the analog to digital converters 627, digital signal processing components 626, and other digital circuits may be separated from the photoactive region of the image sensor 420 and merged together into a processor 426A that is mounted to the substrate 408. Passive components 426P may be mounted to the substrate 408. By separating the image sensor circuit from the processor and passive components, the area of the image sensor under mirrored prism 424 may be devoted to increased pixel density and higher resolution.

Wire bonds 428 electrically couple the image sensor 420 to traces in the substrate 408 to couple the processor 426A and the passive components 426B to each other and to cable bond pads 410. The traces (e.g., see metal layer 508A-508C in FIG. 5) pass under the hermetic seal by way of the ceramic substrate 408 to couple to the cable bond pads 410 outside the hermetically sealed inner housing 404. The cable bond pads 410 may be connected to one or more sheathed cables to receive control signals and power and transmit data along the shaft of the endoscope. The sheathed cables may travel down the length of the surgical instrument and connect the camera module 400 to a surgeon's display console. Alternatively a VCSEL outside the hermetic seal may be mounted to the substrate 408 to transmit data via optical fiber instead of an electrical cable.

CONCLUSION

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed embodiments are limited only by patented claims that follow below.

What is claimed is:

1. A minimally invasive surgical system comprising:
   a patient side manipulator having at least one robotic arm;
   a hermetically sealed endoscopic camera instrument having a housing at a proximal end removably coupled to the at least one robotic arm of the patient side manipulator, the camera instrument further having a hermetically sealed camera sensor at a distal end to capture images of a surgical site, a shaft coupled to the housing, and one or more wristed joints coupled to and between the shaft and the hermetically sealed camera sensor;
   a vision cart having a camera control unit, wherein the camera control unit is coupled in communication with the hermetically sealed camera sensor at the distal end of the camera instrument to capture the images of the surgical site; and
   a monitor coupled in communication with the camera control unit to display the captured images of the surgical site.

2. The minimally invasive surgical system of claim 1, wherein
   the hermetically sealed camera sensor is a stereo camera sensor to capture stereo images; and
   the monitor is a stereo viewer to display the captured stereo images of the surgical site.

3. The minimally invasive surgical system of claim 1, wherein the hermetically sealed endoscopic camera instrument further has
   a plurality of optical fibers routed from the housing, through the shaft, and the wrist and around the hermetically sealed camera sensor to the distal end to provide light in the surgical site; and
   internal sheathed electrical cables routed from the housing, through the shaft, and the wrist to the hermetically sealed camera sensor.

4. The minimally invasive surgical system of claim 3, wherein the vision cart further has
   an illuminator coupled in communication with the plurality of optical fibers to provide the light in the surgical site at the distal end of the hermetically sealed endoscopic camera instrument.

5. The minimally invasive surgical system of claim 4, further comprising
   a light guide coupled between the illuminator and the housing of the hermetically sealed endoscopic camera instrument, wherein the light guide couples the illuminator in communication with one or more of the plurality of optical fibers routed to the distal end to provide light in the surgical site.

6. The minimally invasive surgical system of claim 5, further comprising:
external sheathed electrical cables coupled between the camera control unit and the housing of the hermetically sealed endoscopic camera instrument, wherein one or more of the external sheathed electrical cables couples the camera control unit in communication with one or more of the internal sheathed electrical cables and the hermetically sealed camera sensor at the distal end to capture images of the surgical site.

7. The minimally invasive surgical system of claim 6, wherein
the external sheathed electrical cables coupled between the camera control unit and the housing of the hermetically sealed endoscopic camera instrument are quick disconnect sheathed electrical cables with one or more connectors to facilitate quick disconnect for sterilization.

8. The minimally invasive surgical system of claim 7, wherein
the light guide coupled between the illuminator and the housing of the hermetically sealed endoscopic camera instrument is a quick disconnect light guide with one or more connectors to facilitate quick disconnect for sterilization.

9. The minimally invasive surgical system of claim 6, wherein
the external sheathed electrical cables coupled between the camera control unit and the housing of the hermetically sealed endoscopic camera instrument are quick disconnect sheathed electrical cables with one or more connectors to facilitate quick disconnect for sterilization; and
the light guide coupled between the illuminator and the housing of the hermetically sealed endoscopic camera instrument is a quick disconnect light guide with one or more connectors to facilitate quick disconnect for sterilization.

10. The minimally invasive surgical system of claim 1, further comprising:
external sheathed electrical cables coupled between the camera control unit and the housing of the hermetically sealed endoscopic camera instrument, wherein one or more of the external sheathed electrical cables couples the camera control unit in communication with one or more of the internal sheathed electrical cables and the hermetically sealed camera sensor at the distal end to capture images of the surgical site.

11. The minimally invasive surgical system of claim 1, further comprising:
a master control console coupled in communication with the camera control unit, the at least one robotic arm of the patient side manipulator, and the hermetically sealed endoscopic camera instrument, the master control console to control the camera control unit and the hermetically sealed endoscopic camera instrument in the capture of images of the surgical site.

12. The minimally invasive surgical system of claim 11, wherein
the master control console to further control the at least one robotic arm of the patient side manipulator in the capture of images of the surgical site.

13. The minimally invasive surgical system of claim 11, wherein
the hermetically sealed camera sensor is a stereo camera sensor to capture stereo images;
the master control console includes the monitor coupled in communication with the camera control unit to display the captured images of the surgical site; and
the monitor is a stereo viewer to display captured stereo images of the surgical site.

14. A minimally invasive surgical system comprising:
a hermetically sealed endoscopic camera instrument having a housing at a proximal end removably coupled to a robotic arm of a patient side manipulator, the camera instrument further having a hermetically sealed camera sensor at a distal end to capture images of a surgical site, a shaft coupled to the housing, and one or more wristed joints coupled to and between the shaft and the hermetically sealed camera sensor;
a camera control unit coupled in communication with the hermetically sealed camera sensor at the distal end of the camera instrument to capture the images of the surgical site; and
a monitor coupled in communication with the camera control unit to display the captured images of the surgical site.

15. The minimally invasive surgical system of claim 14, wherein
the hermetically sealed camera sensor is a stereo camera sensor to capture stereo images; and
the monitor is a stereo viewer to display the captured stereo images of the surgical site.

16. The minimally invasive surgical system of claim 14, wherein the hermetically sealed endoscopic camera instrument further has
a plurality of optical fibers routed from the housing, through the shaft, and the wrist and around the hermetically sealed camera sensor to the distal end to provide light in the surgical site; and
internal sheathed electrical cables routed from the housing, through the shaft, and the wrist to the hermetically sealed camera sensor.

17. The minimally invasive surgical system of claim 16, further comprising:
an illuminator coupled in communication with the plurality of optical fibers to provide the light in the surgical site at the distal end of the hermetically sealed endoscopic camera instrument.

18. The minimally invasive surgical system of claim 17, further comprising
a light guide coupled between the illuminator and the housing of the hermetically sealed endoscopic camera instrument, wherein the light guide couples the illuminator in communication with one or more of the plurality of optical fibers routed to the distal end to provide light in the surgical site.

19. The minimally invasive surgical system of claim 18, further comprising:
external sheathed electrical cables coupled between the camera control unit and the housing of the hermetically sealed endoscopic camera instrument, wherein one or more of the external sheathed electrical cables couples the camera control unit in communication with one or more of the internal sheathed electrical cables and the hermetically sealed camera sensor at the distal end to capture images of the surgical site.

20. The minimally invasive surgical system of claim 14, further comprising:
external sheathed electrical cables coupled between the camera control unit and the housing of the hermetically sealed endoscopic camera instrument, wherein one or more of the external sheathed electrical cables couples the camera control unit in communication with one or more of the internal sheathed electrical cables and the hermetically sealed camera sensor at the distal end to capture images of the surgical site.

\* \* \* \* \*